United States Patent [19]
Cox et al.

[11] Patent Number: 6,106,853
[45] Date of Patent: *Aug. 22, 2000

[54] PROCESSES, APPARATUS, AND TREATMENT AGENT/COMPOSITION FOR DEVOLATIZING AND STABILIZING VAPOROUS POLLUTANTS AND THEIR SOURCES

[76] Inventors: James P. Cox; Robert W. Duffy Cox, both of 246 E. Bartlett Rd., Lynden, Wash. 98264

[*] Notice: This patent issued on a continued prosecution application filed under 37 CFR 1.53(d), and is subject to the twenty year patent term provisions of 35 U.S.C. 154(a)(2).

[21] Appl. No.: 08/619,122

[22] Filed: Mar. 20, 1996

Related U.S. Application Data

[63] Continuation of application No. 08/320,561, Oct. 11, 1994, abandoned, which is a continuation of application No. 07/955,489, Oct. 2, 1992, abandoned, which is a continuation-in-part of application No. 07/886,417, May 19, 1992, Pat. No. 5,352,444.

[51] Int. Cl.$^7$ .................................................. A01N 25/02
[52] U.S. Cl. ................. 424/405; 424/409; 424/421; 424/76.2; 424/76.21; 424/76.3; 424/76.5; 424/76.7; 424/76.8; 424/76.9; 424/76.6; 424/661; 424/662; 424/663; 424/664; 424/665; 424/666; 424/723; 514/277; 514/557; 514/724; 514/770; 588/205; 588/237; 588/243; 588/247
[58] Field of Search ..................................... 424/404, 405, 424/409, 613, 616, 76.2, 76.21, 76.3, 76.5, 76.7, 76.8, 76.9, 76.6, 661–666, 723; 588/205, 227, 236, 237, 238, 242–244, 246, 247

[56] References Cited

U.S. PATENT DOCUMENTS

| | | | |
|---|---|---|---|
| 184,700 | 10/1876 | Commins | 424/76.2 |
| 490,797 | 1/1893 | Woolf et al. | 424/76.2 |
| 1,410,249 | 3/1922 | Henderson et al. | 424/76.2 |
| 2,662,855 | 12/1953 | Kamlet | 424/723 |
| 2,689,809 | 9/1954 | Fessler | 424/723 |
| 2,860,050 | 11/1958 | Huff et al. | 424/723 |
| 3,446,893 | 5/1969 | Hanford et al. | 424/76.3 |
| 4,045,316 | 8/1977 | Legan | 204/158 R |
| 4,844,899 | 7/1989 | Juda et al. | 424/664 |
| 5,208,057 | 5/1993 | Greenley et al. | 426/332 |
| 5,389,384 | 2/1995 | Joste | 424/661 |
| 5,527,547 | 6/1996 | Hisht et al. | 424/661 |

FOREIGN PATENT DOCUMENTS

| | | | |
|---|---|---|---|
| 212837 | 3/1987 | European Pat. Off. | 424/76.6 |
| 0427517 | 5/1991 | European Pat. Off. . | |
| 2161741 | 7/1973 | France . | |
| 58-010051 | 1/1983 | Japan | 424/76.6 |
| 2000357 | 1/1987 | Japan | 424/76.6 |
| 2114647 | 5/1987 | Japan | 424/76.6 |
| 1070062 | 3/1989 | Japan | 424/76.6 |
| 1124460 | 5/1989 | Japan | 424/76.6 |
| 1288267 | 11/1989 | Japan | 424/76.6 |
| 2074259 | 3/1990 | Japan | 424/76.6 |

*Primary Examiner*—Neil S. Levy

[57] ABSTRACT

Processes for controlling pollution by: (a) devolatizing vapor phase chemical pollutants (VP's) found in effluents and other bodies and streams of gases and liquids, and (b) stabilizing substrates from which the VP's are released. The offending VP's are converted to less offensive or inoffensive materials by interaction with an appropriately formulated treating agent (VTA/C) containing a primary halogen and at least one additional ingredient selected from the following classes of constituents (optional if bromine is the primary halogen and otherwise required): oligodynamically active metals, cohalogens, adjuncts, and facilitators. The major constituent(s) may be supplied as such, or a source of the constituent may be provided. Actinic radiation can be employed to promote reactions between the VP and the VTA/C, which is often formulated as an aqueous scrubbing medium. The VTA/C may, however, be employed in other ways—for example: (a) by gaseous infusion into a reaction zone; (b) by dusting or coating the treating agent onto, or otherwise directly adding it to, a substrate prone to evolve VP's to control the emission of VP's from the substrate; or (c) by impregnating it into an activated carbon carrier.

3 Claims, 7 Drawing Sheets

ACTINIC RADIATION- EXTERNAL SOURCE

122

123
123
122

PROCESSES, APPARATUS, AND TREATMENT AGENT/COMPOSITION FOR DEVOLATIZING AND STABILIZING VAPOROUS POLLUTANTS AND THEIR SOURCES

This application is a continuation of application Ser. No. 08/320,561, now abandoned, filed Oct. 11, 1994, which is a continuation of application Ser. No. 07/955,489, now abandoned, filed Oct. 2, 1992, which is a continuation-in-part of application Serial No. 07/886,417 U.S. Pat. No. 5,352,444 filed May 19, 1992, the benefit of the filing dates of which are hereby claimed under 35 USC 120.

TECHNICAL FIELD OF THE INVENTION

The present invention relates to novel processes, apparatus, and treatment agents for purifying air, other gases, and liquids containing vapor phase pollutants and for stabilizing the substrates from which the pollutants are released.

The pollution of air may currently be of the most concern, and the principles of the present invention will accordingly be developed principally in relation to the removal of offending pollutants from air. It is to be understood, however, that this is being done for the sake of convenience and clarity and is not intended to limit the scope of the invention as defined in the appended claims.

However achieved, primary aims of the invention are the devolatization and stabilization of the pollutants and their sources to keep the pollutants from spreading beyond the environment in which they are found. Mechanisms that may be involved include: addition reactions, polymerization, decomposition, absorption and adsorption, physical entrapment, and chemical complexing and decomplexing.

In many cases, another goal of the invention is to retain, create, or enhance the value of the pollutant.

DEFINITIONS

Vaporous Pollutant (VP): Any vapor or other gas or an aerosol, colloid, or other dispersion with a gaseous phase and one or more constituents which are threats to plant and animal life and/or to the environment. The vaporous pollutant does not necessarily have to be both noticeable and noxious. It may be an inorganic substance such as carbon monoxide, hydrogen sulfide, a nitrogen oxide, or an ammonium compound or any of a host of organic pollutants including hydrocarbons of all classes and compositions with nitrogen-, sulfur-, and halogen-containing moieties.

Vapor Treating Agent/Composition (VTA/C): an agent or composition which is formulated in accord with the principles of the present invention and is capable of so interacting with a VP in an extensive variety of settings as to devolatilize at least a portion of the VP in a gas or liquid stream, the atmosphere, or a body of gas or liquid in which the pollutant is present. The VTA/C may also have a beneficial stabilizing effect on the VP and/or the substrate from which the VP is released. As used herein, VTA/C and the term "etreatment agent" are equivalent.

Primary halogen: any halogen except astatine used solely or in the greater proportion as a VTA/C ingredient. Bromine, fluorine, and iodine may be used alone as a primary VTA/C halogen while all halogens including chlorine may be used in combination with cohalogens or other VTA/C ingredients as primary halogens. Bromine is the preferred primary halogen for VTA/C'S containing a single halogen. Chlorine and bromine are preferred if a cohalogen is to be employed.

Cohalogen: a halogen which can be combined with a primary halogen to provide a combination that is synergistically effective in the devolatization of VP's and the stabilization of VP sources. Bromine is the preferred cohalogen when chlorine or fluorine is the primary halogen although iodine can be employed as the cohalogen.

Source: (1) that which releases a VP, or (2) a compound or composition which releases a primary halogen or cohalogen, an oligodynamic metal, or other VTA/C constituent to the reaction zone in the course of a treatment employing the principles of the present invention.

Oligodynamic Metal: Selected metals which, when included in of VTA/C's in small concentrations, endow them with a profound capacity to control pollution from VP's OR VP sources. Oligodynamic metals may be employed in VTA/C'S in elemental, ionic, or combined form. VTA/C's containing oligodynamic metals or metal sources usually have substantially improved activity when associated or present with a primary halogen, a cohalogen, an adjunct, or a facilitator such as an initiator or a free radical, particularly when the VP contains significant amounts of hydrocarbons.

Adjunct: a VTA/C constituent which has surfactant and/or solvent capabilities and makes a VTA/C more effective by wetting a VP substrate, facilitating penetration of the substrate or interaction between the substrate and the VTA/C, or otherwise improving or extending contact between the VTA/C and the substrate or between the VTA/C and the VP or VP source.

Facilitator: A constituent or additive which activates or otherwise significantly improves the effectiveness of a VTA/C.

Substrate: matter which may contain or generate VP's or which may combine with other matter to release VP's.

Photosensitized: VTA/C constituents which exhibit increased reactivity in the presence of radiant energy, resulting in more rapid and more complete devolatization reactions or interactions between the VTA/C and the VP being treated. Photosensitization usually involves the formation of ionic species or free radicals from oxygen or oxygen-containing molecules present in or supplied to the reaction zone.

Augmented halogen: any halogen which is intrinsically photosensitized or has been photosensitized prior to or during VTA/C treatment of a VP or which is otherwise augmented—e.g., with an oligodynamic metal, a facilitator, an adjunct, or a cohalogen.

BACKGROUND OF THE INVENTION

VP's are major air pollutants. Authorities have taken steps to combat VP pollution by promulgating and enforcing regulations designed to effect major reductions in the quantities of those substances released to the surrounding environment. Current control statutes are mostly unrealistic. Attempted enforcement and compliance with these statutes is creating monumental difficulties.

The pollution control industry in its current form is of relatively recent origin and does not have an adequate inventory of cohesive systems or techniques with which to meet many of the new mandatory requirements. Indeed, it is not unusual for little or no improvement whatsoever to result from expanded application of known pollution control equipment using traditionally acceptable chemical treating agents. Sometimes, the result is a worsening of the situation, the only constant to date being an unremitting economic loss hidden in inflated costs of American-produced goods.

Scrubbing systems are perceived as perhaps the best currently available for VP control. A typical effluent scrubbing system today uses essential oils to provide a so-called vapor phase reaction. While this has correctly never been viewed by competent persons as an appropriate primary control step, additions of aromatics and essential oils are being promoted and actually used as controls for VP emissions. This only modifies human olfactory responses to some VP's. It does not rid the environment of VP's or otherwise remediate the damage caused by the release of VP's to the environment.

There are difficulties, too, in applying other techniques used in the past for the treatment of VP's—reaction of the offending VP with hydrogen peroxide, chlorine, or chlorine dioxide being typical examples. These materials are limited in application and can create as many or more problems than they can solve. For example, adding hydrogen peroxide to styrene resin vapors, a ubiquitous and troublesome VP, might provide realistic reductions in air effluents but not without creating significant problems such as increased explosion and fire hazards.

Compounding the problem is the enormous number of chemical species that are involved.

The plastic industry generates considerable air pollution in the form of resin vapors and solvents such as acetone, methyl ethyl ketone, and others.

It is common for chlorine to be proposed as a control for these and other VP's. Typically, chlorine is at best no more than marginally effective. In some cases, it actually exacerbates the problem by producing partially chlorinated effluents which may have a worse impact on the environment than the untreated products.

Chlorine is also widely and somewhat effectively employed for the removal of biological volatiles such as those generated by rendering, food processing, sewage, sludge, and such. Chlorine, however, is not very effective against most VP's including styrene and similar resins, phenols, terpenes, sesquiterpenes, petroleum, asphalt tars, and many other aliphatic and cyclic hydrocarbons.

Wood products evolve VP's during kiln and other forms of drying. The effluent can contain a wide variety of terpene- and terpenoid-type VP's.

Typical are southeastern pine shavings or chips. These wood products are used for making particle board. In this particular process, wood chips are dried in a rotary kiln. Once the chips have been conditioned by drying, they are subjected to processes which convert them into sheet board stock. This procedure is proprietary but involves the addition of adhesives and fillers to the chips and the subsequent formation of the treated chips into the completed products.

During chip drying, water is driven from the chips; and volatiles are more-or-less simultaneously driven off the chips with the water. Analysis of the emissions shows that alpha- and beta-pinenes, l-limonene, and camphene are principal components. All of these compounds are terpenes, and all are VP's.

Different tests using proven designs such as countercurrent and reverse spray or jet scrubbers charged with aqueous suspensions of more-or-less conventional scrubbing solutions containing chlorine, chlorine dioxide, potassium and sodium hydroxides, potassium permanganate, hydrogen peroxide, ozone, and the like have demonstrated little if any reductions in VP process effluents generated in the forementioned and other types of wood product production.

VP's originating from biological processes and biowastes have become increasingly more difficult to treat as volumes have grown to enormous proportions in some locales. Sewage; sludge; municipal solid and sanitary wastes; and food, fish, meat, agricultural, compost, and related processing have become very intensive, creating new problems characterized by increased volumes, complex blends and mixtures, and handling restrictions.

Traditional control systems in many cases are only marginally effective against these pollution sources. In other cases, useful control techniques and systems are simply not available.

While scrubbing is perhaps the technique most often used for removing pollutants from gases, the use of zeolites for this purpose has also been proposed. Zeolites are hydrated aluminum and calcium or sodium silicates—characteristically porous solids which require "activation" to become effective. Referred to as molecular sieves, zeolites are to different degrees effective in a variety of applications involving the treatment of volatile organic compounds.

Thus, U.S. Pat. No. 2,921,970 proposes the use of a single, contiguous, gravitating bed of zeolites for sorbing and separating into different zones hydrocarbons of differing weight. The proposed system attempts to overcome the cumbersomeness of dealing with a bed of solids under practical conditions with a polyvalent, cationic, silicate complex.

U.S. Pat. No. 2,944,033 discloses the use of insoluble exchange resins made from non-halogenated copolymers of styrene and maleic anhydride crosslinked with diamines in oxidizing various chemical compositions.

U.S. Pat. Nos. 2,988,502; 2,952,630; and 2,950,336 are concerned with similar products and systems for capturing, separating, and treating aromatic, paraffinic, and other hydrocarbons utilizing a number of different zeolites. Naturally occurring zeolites such as chabazite and analcite and synthetic zeolites are proposed.

U.S. Pat. No. 3,676,330 discloses an improved composite of a zeolite and a coating material for use as a catalyst. U.S. Pat. No. 3,719,026 proposes the use of an aluminum deficient zeolite in extracting non-polar substances from mixtures of polar and non-polar substances.

U.S. Pat. No. 4,309,281 discloses a calcined zeolite for separating non-aromatic compounds from aromatic compounds. U.S. Pat. No. 4,425,143 proposes yet another zeolite-based technique for removing impurities from gases. U.S. Pat. No. 4,529,416 discloses the use of sodium mordenite pellets in adsorption columns.

U.S. Pat. No. 4,564,604 is concerned with a catalyst comprised of protonized zeolite. This catalyst is claimed to be effective against oxides of nitrogen if they are washed with ammonia before passing across the catalyst. U.S. Pat. No. 4,544,378 proposes that faujasite-containing compositions be used for this same purpose.

Most of these patented applications require sorption and desorption cycles, activation of the zeolite, and complex zoned beds. They present difficulties with plugging and in keeping the bed at the more-or-less precise temperature needed for efficient operation. As a result, none of these patented techniques are practical for effluent control. Also, capital, operational, and maintenance expenses are prohibitive. Moreover, the efficiencies required for the applications to be practical in the real world are, with certain notable exceptions, all but impossible to accomplish within economic limits.

Still other techniques for separating out VP's are disclosed in the patent literature.

U.S. Pat. No. 3,403,498 discloses a method for removing saponifiable foreign substances from a gas stream by directing the effluent through a labyrinth. It is stated that saponifiable substances will collect by impingement on the labyrinth structure. The collected materials are then removed from the labyrinth with a caustic soda solution.

Proposed in U.S. Pat. No. 4,528,001 is the recovery of volatile organic matter from gases and gas mixtures via gas/liquid contact with an aqueous system. That system includes a hemiether or hemiester of an polyalkylenepolyol. A two-step process designed to recover resources and prevent pollution is employed.

U.S. Pat. No. 4,426,210 discloses a process for scrubbing odorous effluents with a solution of polyethylene glycol sorbitan laurate or an ester of sorbitan with palmitic acid and water. This process is said to be capable of effectively eliminating many volatile organic compounds from process effluents.

While the foregoing patents address the problem of cleaning effluent streams contaminated with VP'S, few are of any practical use in pollution control. They are limited by capital, operational, and maintenance requirements and exhibit impracticalities such as low efficiency attributable to bleed through, clogging, and surface plugging.

U.S. Pat. Nos. 2,492,085 and 2,906,668 disclose compositions containing aluminum chlorohydrate, zirconyl, aluminum halohydroxy complexes. The patented compositions are intended to be used as personal body deodorants and antiperspirants (the use of these compositions and complexes for VP control has not been proposed).

Another process that makes use of chlorinated compounds and which can also be employed in removing pollutants from air streams is disclosed in U.S. Pat. No. 4,844,721. That patented process, however, requires a scrubbing medium which contains a drying or semidrying oil with a high iodine value. The requirement for such oils in high concentrations can make the scrubbing medium too expensive for many VP control applications. Also, this patent is concerned with the recovery and regeneration of scrubbing media and not the devolatization of pollutants.

While ultraviolet radiation and air may be of some benefit in separating collected pollutants from treating media, they also accelerate polymerization and oxidative degradation of the treating oils used for scrubbing out pollutants. This reduces the efficiency of the medium and forms resinous masses and coatings which require frequent and difficult treatment. This can also make it more difficult to separate and handle recovered pollutants.

In short, the present day pollution problems attributable to VP's are pervasive and of enormous magnitude. Available techniques for combatting these problems are only marginally effective at best; and there are associated with available VP control techniques such other drawbacks as high capital, operating, and maintenance costs and the generation of products which are themselves pollutants.

SUMMARY OF THE INVENTION

There have now been invented and disclosed herein certain novel, improved processes which employ halogen-based treatment agents and which are capable of effectively treating without the problems discussed above a wide variety of VP's including heretofore treatment-resistant cyclic hydrocarbons.

Controlled by the techniques disclosed herein is pollution attributable to, inter alia: (a) many volatile molecules containing nitrogen, sulfur, and carboxyl groups including lipid breakdown products of fatty acids; primary, secondary, and tertiary amines; thiophenes; and carboxyls; (b) those and other VP's from different kinds of processes such as thermal, aeration, fermentation, composting, and the digesting of biological matter including biological wastes; (c) volatile effluents from resins, paint booths, and plastics and rubber manufacturing including terpenes, terpenoids, and polyterpenes; (d) vapors released from asphalt tars, styrene and other resins, and crude oils; (e) hydrocarbons; and (f) inorganic compounds including carbon monoxide, hydrogen sulfide, sulfur dioxide, ammonia, and nitrogen oxides.

The present invention is particularly important because of its effectiveness against many volatiles released from biological matter including those released in and from bioprocessing and biowastes. This effectiveness is seen even in those instances where the volatiles from bioprocessing or biowastes include vapor phase complexes of mixed biological and hydrocarbon character.

Hydrocarbons are, as a rule, much more resistant to treatment than pollutants of biological origin. The present invention is effective against many hydrocarbons including alkanes, olefins, alkynes, alkadienes, and cyclic hydrocarbons. Representative of those hydrocarbons which can be effectively treated by employing the principles of the present invention are: monocyclic, bicyclic, and acyclic terpenes; sesquiterpenes; terpenoids; isoprene monomers and polymers and other hemiterpenes; cycloparaffins including cyclopentane, cyclohexane, cyclopentadiene, and cyclooctatetraene; benzenes including styrene monomers and polymers; naphthalenes and anthracenes; and the hydrocarbon constituents of asphalts, petroleum products, and other native hydrocarbons.

The invention can also be used to particular advantage to effectively treat heterocyclic compounds such as pyridines; lipid breakdown products of fatty acids; fatty acid residues; and volatile nitrogen- and sulfur-containing compounds derived from biological matter including protein breakdown products, peptides, peptones, and primary and secondary amines.

As indicated previously, complex combinations of VP'S can also be rendered harmless by employing the principles of the present invention. Combinations of VP's amenable to treatment are found in emissions from, as examples: asphalt tars; plastics; rubber; phenolic and other resins, crude petroleum; paint; pulp and paper; particle, press, and chip boards; kerosene; gasoline; and composts.

Many other emissions heretofore unamenable or only partially amenable to treatment may also be effectively remediated by the present invention.

The treatment agents of the present invention are readily applied to the offending VP's in a scrubber. They may also be applied through spray nozzles; used in conjunction with filters or in bag houses and other contact appliances; and added directly to the VP's or the source of the VP's—for example, to a waste water stream, a sewage or sludge line, a well head, an effluent, emissions from food processing operations including those generated in restaurant and other kitchens, a dissolved air flotation cell, a leachate pond, or other substrate.

DETAILED DESCRIPTION OF THE INVENTION

Figure 1:
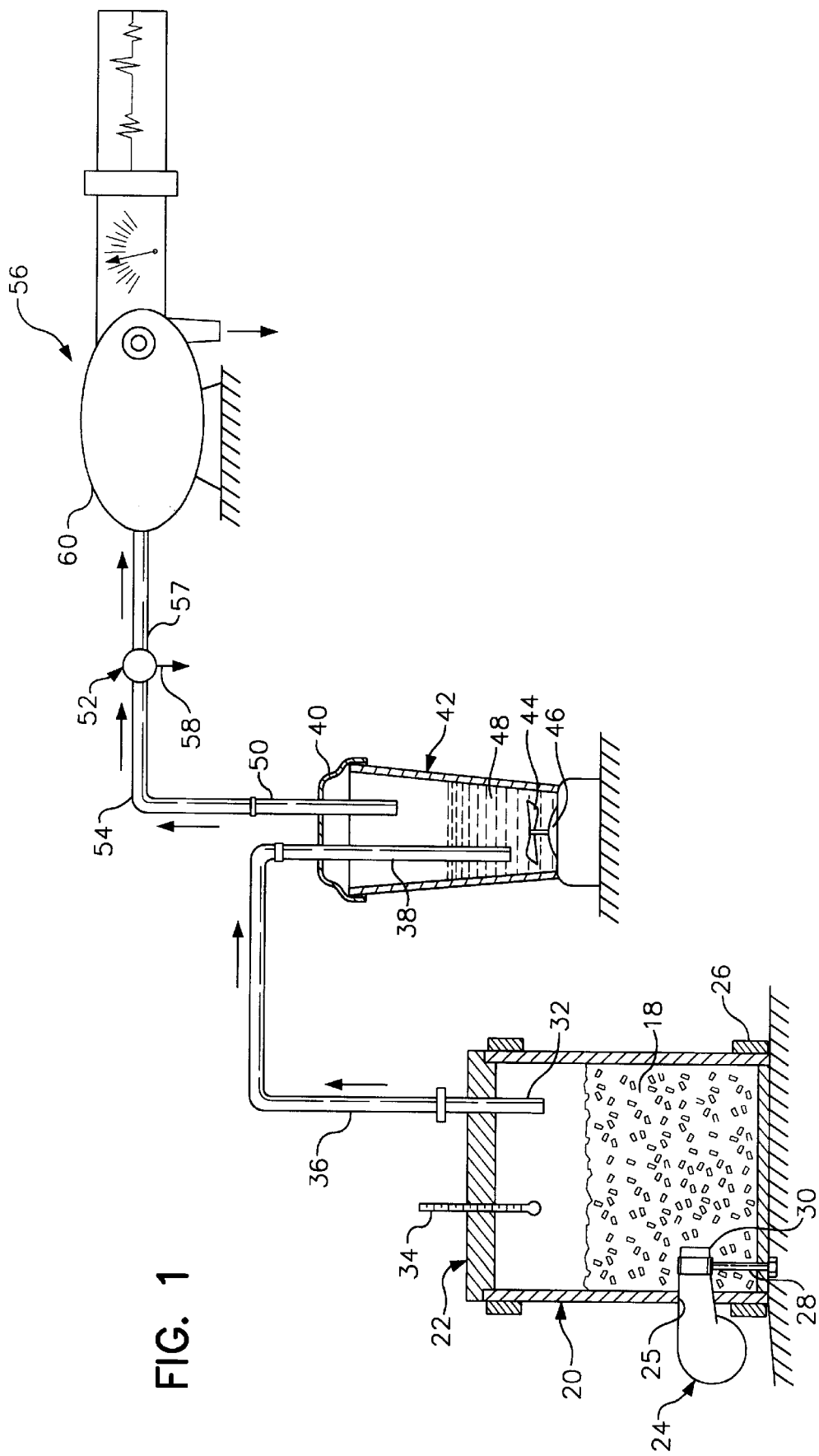
FIG. 1 is a somewhat simplified schematic of one system for eliminating VP's from effluents in accord with the principles of the present invention.

The adverse effects of VP's' amenable to treatment by the techniques disclosed herein in terms of pollution are well established. Sulfur-containing VP's such as thiophenes, for example, pose a particular problem, especially when they are encountered as components of those complex of fgases generated in food and agricultural processes and more notably in pulp and paper processing. They are almost always olfactorily prominent if not always noxious. Nitrogen compositions such as primary, secondary, and tertiary amines have a strong aromatic, even pungent character. Carbon monoxide is a well-known and prevalent atmospheric pollutant which is noxious but not malodorous. The foregoing VP's are ubiquitous and frequently unamenable to conventional control techniques.

Other VP's that have proven particularly intransigent to treatment are hydrocarbon components of asphalt and coal tars; emissions from crude oils and fractions thereof such as gasoline; naphthalene; toluene; xylene; anthracene; benzene; butyl benzene; cymene; cumene; pinene; limonene; ethylene; propene; phenol; bisphenol; cresols; phenolics; styrene, SBR, ABS, and SAN resins; styrenated polyesters and copolymers; epoxy, butadiene, acronitrile, and other resins; methane; alcohols; phenols; ethers; carboxylic acid derivatives; carbonyls; aldehydes; and aliphatic and cyclic compounds including many containing sulfur, nitrogen, and/ or oxygen. These and many other VP's are commonly found in complex mixtures such as the emissions from crude petroleum, asphalt, coal tars, and biological wastes; in effluent streams from wood product processes such as pulp and paper manufacture and wood chip drying; and in the manufacture and use of synthetic resins.

The above-discussed and other VP's can be effectively, safely, and economically reduced in concentration or even entirely eliminated from offgas and other effluents by contacting the offending VP's with the novel treatment agents referred to in this specification as VTA/C's.

The primary active principles of the simplest but nevertheless effective VTA/C's disclosed herein are:

A) bromine; or

B) bromine, chlorine, iodine, or fluorine and at least one of the following:
 1) one or more cohalogens or cohalogen sources;
 2) one or more oligodynamic (or oligodynamically active) metals or metal sources;
 3) one or more surfactant/solvent adjuncts or adjunct sources; or
 4) one or more facilitators or facilitator sources.

In treating more intransigent VP pollutants, the VTA/C is formulated to include bromine (preferred) or chlorine and at least two of the following:

1) one or more cohalogens or cohalogen sources;
2) one or more oligodynamically active metals or metal sources;
3) one or more adjuncts or adjunct sources; and
4) one or more facilitators or sources thereof.

The foregoing active VTA/C constituents may be distributed in a carrier which is frequently but not always water. The substrate with which a VTA/C is contacted may in some cases act as a carrier. Other carriers include gases such as the allotropes of oxygen, carbon dioxide, and nitrogen and potentially interactive gases or vapors including sulfur, chlorine, and bromine dioxides. The carrier may also be a liquid such as an alcohol or a carboxylic or other acid such as acetic.

Irrespective of whether bromine, chlorine, iodine, or fluorine is employed as the primary halogen in a particular VTA/C, the halogen is most effective if it is intentionally dissociated to promote VTA/C-VP reactions. Sometimes the VP'S to be treated will provide dissociation forces and sometimes VP components, interaction intermediates, equipment, or treating zone conditions will. Otherwise, the primary halogen may be disassociated chemically, thermally, photolytically, by gamma radiation, by peroxides, by actinic radiation, or by contact with an active form of oxygen such as atomic or molecular oxygen or ozone. An activator may, in many cases, even be present at some point in the substrate or effluent stream being treated.

Bromine is preferred when a cohalogen is not employed. It may be supplied in elemental form or by way of a bromine source compound. Useful compounds include bromites, bromates, bromides, bromine oxides, hypobromites, bromine halides, bromine-containing acids, metallobromines, and bromamides. Representative specific bromine sources include: ammonium and other non-metallic bromides; silver bromide; hydrogen bromide; hydrobromic acid; bromoacetic acid; bromobutyric acid; lithium bromide; potassium bromide; sodium bromide; alkali earth metal bromides including calcium bromide; alkali metal hypobromites; zinc bromide; phosphorous bromide and tribromide; bromine trifluoride; aluminum, cupric, cuprous, ferric, ferrous, cobaltic, and cobaltous bromides, bromates, and bromites; bromine chloride and iodide; iodine bromide; other monovalent bromides; bromous and hydrobromous acids; sodium bromite; bromic acid; sodium bromate; aluminum bromate; potassium bromate; barium bromate; bromamides; nitrogen bromide; bromine dioxide; brominated oils; bromine pentafluoride and trifluoride; and combinations, derivatives, or complexes of the foregoing compounds.

As is discussed in detail below, the effectiveness of bromine as a VTA/C may be substantially enhanced, in terms of the consistent pollution reduction of different VP's, by varying the pH in the VTA/C-VP reaction zone. An even greater effect on efficiency may be had by adding small concentrations of surfactants or solvents to the bromine-based VTA/C.

There are many applications of the present invention in which a controlled release of the bromine from the source compound is wanted so that the VTA/C will remain active over an extended period of time. Such applications include those in which the VTA/C is applied to a substrate to treat offending VP's as they continue to evolve from the substrate. Controlled release sources of bromine include:

bromine liquid, brominated oils, 1-bromo-3-chloro-5,5-dimethyldantoin, n-bromosuccinimide, dibromomethylhydantoin, dioxane dibromide, pyridine hydrobromide dibromide, and various quaternary ammonium polybromides.

A highly viable alternative for making bromine available over an extended period of time is the in situ generation of the bromine from a bromide and a mineral acid. Preferred are sodium bromide and sulfuric acid.

Preferred bromine sources are:

Gas: elemental bromine

Liquid: hydrobromic acid and elemental bromine Controlled release: 1-bromo-3-chloro-5,5-dimethylhydantoin For use with actinic radiation: para-chlorophenylmagnesium bromide Hydrobromic acid more often enhances and in some cases fulfills the minimum necessity for a VTA/C, particularly in the treatment of simpler volatile effluents. In the case of more resistant VP's, it may nevertheless generally be expected to prove more effective when a cohalogen is added.

Other effective bromine sources, especially when bromine is the sole halide, are metallobromines containing aluminum, cobalt, copper, iron, magnesium, and zinc. Grignard reagents, particularly those with an alkyl group such as ethylmagnesium bromide are particularly useful as bromine sources in VTA/C's.

When chlorine is the primary halogen, bromine is frequently the preferred cohalogen. Bromine chloride and iodine bromide are representative of other cohalogens which can be used to advantage when chlorine is the primary halogen.

Those bromine-containing VTA/C's designed for treating VP's containing substantial portions of aromatic hydrocarbons with nitro or alkyl substituents perform more effectively when a Lewis acid is added to the VTA/C. When the VP's being treated are comprised principally of activated aromatic compounds such as phenols, anilines, and aromatic ethers, a Lewis acid or oligodynamic metal may not be needed to provide substantial VP devolatization.

VTA/C's containing bromine supplied by n-bromo compounds such as n-bromosuccinimide and 1,3-dibromo-5,5-dimethylhydantoin perform well in the treatment of hydrocarbon compounds containing acyclic and benzylic moieties. VTA/C's with phosphorous moieties such as phosphorus tribromide or triphenylphosphonium dibromide as the bromine source are particularly effective against alcohols.

The VTA/C's disclosed herein effect the replacement of the chlorine atoms of many chlorinated hydrocarbons, especially if they contain Lewis acids or phase transfer catalysts. These VTA/C's are particularly effective in reducing the pollution attributable to chlorinated VP'S. Bromine-containing VTA/C's are also particularly effective for treating volatiles containing aldehydes, ketones, carboxylic acids, and active methylene radicals.

Where cost and safety factors permit, fluorine may replace bromine as a sole and primary halogen. Iodine can also be used in this way, but it is seldom as effective as bromine or fluorine.

As suggested above, the reaction of the halogen(s) in a VTA/C in the presence of an oligodynamic metal is of particular importance in the treatment of many VP pollutants. Oligodynamic metals are also important because they can be amminated; coordinated with monodentate, multidentate and even bridgehead ligands; or in some instances used amphoterically to provide VTA/C suspensions.

Ammonia and ammonium compounds may be employed as partitioning agents to shield interactive VTA/C components while they are in solution together. Upon application of the VTA/C the ammonia or ammonium compound evaporates, falling below the critical level required for it to act as a partitioning agent. The VTA/C ingredients are then free to react with the substrate.

In VTAC's using metals in higher ionic states, an antioxidant such as citric acid or sodium bisulfite can be added to provide an additional degree of VTA/C solution stability.

Other methods of providing event-deactivated partitions employ amphoteric metals or amphoteric metal compounds and compatible solvents or surfactants. A simple, exemplary, event sensitive partition uses a basic Bordeaux mixture containing copper sulfate (an oligodynamic metal source) and hydrated lime as a VTA/C ingredient. Subsequent to application, this portion of the VTA/C becomes slowly active as the copper/lime colloid is dried into a film. At this point soluble copper is formed over time as the calcium carbonate dissociates. This can happen very quickly if the conditions for dissociation are optimal as they sometimes are in pollutant treatment zones.

One functional pathway by which oligodynamic metals devolatize pollutants involves the formation of ammines and mono and multidentate coordination complexes, at least some portions of which are organic decomposition type VP's. Varying degrees of inclusion of an oligodynamic metal also permits the formation of VTA/C suspensions which would be otherwise difficult —if not impossible—to form, providing a product which does not readily separate. When used to provide this benefit in a VTA/C, the oligodynamic metal should be one which is not adversely influenced by the suspension or partitioning additive(s) but should also be selected for its ability to participate in the devolatization of VP's.

Depending on the particular VP or VP complex being treated and the treatment conditions, the oligodynamic metals in VTA/C's may interact in many other ways to efficiently devolatize VP's. Among the many known functions of the oligodynamic metal which may come into play independently or in sequence are its abilities to act as: a catalyst, initiator or other reaction promoter; a Lewis acid; a Brønsted acid; an ion acceptor; an adduct former; a ligand; a sequestrant; a floccing agent; a cross-linking agent; an electrophile; and a clathrant, chelant, or inclusion complex participant for forming the above-mentioned ammines and mono, multi or bridgehead dentates or other coordination compounds and, in some cases, intercalation compounds. Ammines are formed by union of ammonia with an oligodynamic metal in such a way that nitrogen atoms instead of carbon atoms are linked directly to the metal. This is important because of the often resulting marked devolatization of the offending VP that is obtained, especially where ammonia, amines, or other sensitive forms of nitrogen are present.

In short, oligodynamic metal-containing VTA/C's may be effective in the treatment of VP's by one or many pathways followed sequentially, more or less simultaneously, or randomly. By whatever means it operates, a VTA/C containing an oligodynamic metal can provide effective and sometimes profound control of many simple and complex VP's.

Those metals which are oligodynamically active in VTA/C's are: aluminum, cerium, titanium, molybdenum, copper, zinc, tin, zirconium, iron, silver, magnesium, manganese, nickel, chromium, cobalt, thorium, cadmium, vanadium, and bismuth. Disregarding advantageous combinations but not potential toxicological considerations of oligodynamic metals, a general, descending order of preference for use in many VTA/C's—depending somewhat on the particular application—is: aluminum, iron, zinc, copper, cobalt, zirconium, cerium, and silver. The metals in groups 6, 7, 8, 9, 10, 11, and 12 of the periodic system (see Hägg, General and Inorganic Chemistry; John Wiley & Sons, Inc., New York, N.Y.; 1969; PP. 90–93); those non-transition metals of group 13; and the actinide thorium are potentially the most effective.

Boron is the oligodynamically functional equivalent of the metals identified in the preceding paragraph. For that reason and for convenience, boron will be subsumed herein under the heading oligodynamic (or oligodynamically active) metal even though it is not a true metal.

For different VP's, the preferred oligodynamically active metals are:

| Type of VP | Oligodynamically active metal |
|---|---|
| Organic other than hydrocarbon | Iron, copper, zinc |
| Acidic and composed primarily of hydrocarbons | Boron, aluminum, cobalt |
| Alkaline | Aluminum, copper, zinc, zirconium, or tin: an amphoteric metal compound such as manganese hydroxide or titanium dioxide; boron; or magnesium |
| Neutral or slightly alkaline or acidic | Manganese, zinc, aluminum |
| Organic, acidic, and low hydrocarbon content | Boron, iron, copper, silver |

The other metals listed above may be useful as a cometal or in specific applications discussed elsewhere in this specification.

The oligodynamic metal may be added to the VTA/C in elemental form, or a source of the metal may be employed. Suitable sources include: ores, scrap metals, Lewis acids, and other compounds and complexes —for example, zinc bromide, zinc chloride, aluminum bromide, aluminum ammonium sulfate, aluminum chloride, aluminum borate, aluminum acetate, aluminum benzoate, aluminum chlorate, aluminum hydride, aluminum hydroxide, aluminum iodide, aluminum nitrite, aluminum sulfate, aluminum chlorohydrate, cupric and cuprous chlorides and bromides, cupric fluoride, ferric bromide, ferric chloride, ferric oxide, ferric sulfate, cobaltous ammonium sulfate, cobaltous bromide, cobaltous bromate, cobaltous chloride, cobaltous fluoride, and cobaltous iodide.

VTA/C's containing oligodynamic molybdenum and surfactant type adjuncts interact with propylene and other VP fractions when an organic peroxide is available to give propylene oxide and other oxides. These oxides transitionally interact with many VP fractions, yielding reaction compounds in states which facilitate further pollution reducing treatment and collection from liquid scrubbing media.

VP's containing toluene, para-xylene, and other hydrocarbons may be converted by VTA/C's containing surfactant adjuncts of amminated oligodynamic metals (preferably cobalt, cerium or aluminum) to benzoic and terephthalic acids when a peroxide and/or actinic light is available to the reaction. Similarly, oligodynamic metals (preferably iron, cobalt, or manganese) are effective against VP's containing isopropylbenzene, coal tar, naphtha, and nahthalenic volatiles and homologues thereof, whereas oligodynamically active copper, cobalt, iron, and manganese are preferred when $C_{10}$ hydrocarbons such as cumene are components of the VP to be treated.

VTA/C's containing copper, cobalt, cerium, zinc, manganese, and iron are preferred in VTA/C's formulated for treating VP's containing 1,3,5-trimethylcyclohexane, methyl methacrylate, and analogous compounds. Zirconium is the preferred oligodynamic metal when formaldehyde is encountered. In general, VTA/C's containing cobalt, vanadium, tin, and zinc are preferred for treating VP emissions containing unsaturated polyesters and prepolymers such as poly(dimethyl siloxane) and epoxy resin volatiles.

A cohalogen can often be employed to advantage in a VTA/C as disclosed herein even if bromine is employed as the primary halogen; and a cohalogen or other augmenting constituent is often essential if bromine is not the primary halogen. More broadly, a halogen other than bromine can be employed as the primary halogen in a VTA/C if an oligodynamic metal, cohalogen, adjunct or facilitator is present in the VTA/C, even if the halogen is by itself not effective. The appropriate augmenting constituent is empirically determined on a case-by-case basis as experiences to date often do not permit reliable VTA/C's for specific complex VP's to be formulated otherwise, except in the most general way. However, the principles and techniques disclose in this specification provide approaches for efficiently working up VTA/C's which can be used to effectively treat most VP's.

Simple—halogen (bromine or chlorine) plus oligodynamic metal—VTA/C's are particularly effective in the treatment of biological volatiles containing more-or-less pure, or high, concentrations of VP'S which are lipid and protein breakdown products such as carboxylic acids and/or amines. In some instances, metal chlorides may work as well or better than bromine or bromine compounds in these applications of the invention.

In those few case where bromine is inadequate by itself, fluorine, chlorine, and iodine are all suitable cohalogens; and bromine, fluorine, and iodine can be used as cohalogens with chlorine.

Cohalogen constituents for VTA/C's may be supplied in elemental form or in compositions which may often advantageously include oligodynamically effective metals. Grignard reagents and alkyl Grignard reagents are good examples of the latter.

Elemental chlorine and its salts are generally though not always the preferred cohalogen sources in those formulations employing bromine as the primary halogen. Iodine or an iodine salt may be more effective under some specific circumstances but is preferably avoided when the VP to be treated contains substantial quantities of paraffins. Iodine has been seen to interfere with the efficiency of VTA/C's in applications where paraffinic hydrocarbons are present.

As a cohalogen for VTA/C'S used against VP's containing unsaturated aliphatic compounds, iodine is about as effective as chlorine. However, a VTA/C comprised of hydrogen bromide or chloride or a comparable bromine or chlorine compound and an acid such as sulfuric in significant concentrations provides a more dependable and faster VTA/C-VP reaction, even at those relatively low ordinary temperatures (up to the boiling point of water); and many chemical reactions proceed too slowly to be practical in a typical pollution control setting, if at all.

Bromine-containing VTA/C's are efficient in the devolatization of many aromatic hydrocarbons when the cohalogen chlorine is present but are usually less so when the cohalogen is iodine. The removal of aromatic VP's with VTA/C's containing bromine chloride are much faster than when bromine alone is used. VTA/C's containing bromine also have the advantage that organic solvents can readily be used as carriers. Applications in which this is important include those involving the treatment of many hydrocarbons, particularly cyclic hydrocarbons.

The solubility in water of bromine constituents is improved when a cohalogen such as chlorine is present due to the concomitant presence of chloride ions. This is important as water is often the preferred carrier for a VTA/C because of its low cost, widespread availability, lack of toxicity, ability to remain in the liquid phase over a wide range of commonly encountered process conditions, and other desirable attributes.

VP's which are carboxylic acids or oxidative degradation products of lipids, many amines, and other VP's—particularly those released from biological substrates and aliphatic and cyclic hydrocarbons—can frequently be treated to advantage with VTA/C's which are, or contain, an oligodynamic metal and a halogen (bromine or chlorine) in combined form. Aluminum, zirconium, cobalt, copper, zinc, iron, silver, and other of the oligodynamic metals identified above may be combined with halogens for this purpose. The following oligodynamic metallohalogen compounds and complexes are representative of those that can be employed.

aluminum perchlorate, aluminum chloride, aluminum chloride hexahydrate, aluminum chlorohydrate, aluminum bromohydrate, aluminum hydroxychloride, a complex of the formula $(Al)_l(OH)_m(Cl)_n$, where m=2–2.5, n=0.5–1, and the total of l, m, and n is 3, zirconium dichloride or dibromide, zirconium tribromide or trichloride, zirconium tetrachloride or tetrabromide, and zirconium oxychloride or oxybromide.

Halogenated aluminum, cobalt, and zinc compounds and complexes such as chlorides and bromides, for example, are particularly effective against α-pinene, β-pinene, limonene, and camphene, interacting with these compounds to form readily recoverable complexes which are typically economically valuable resins. These resins (and resins produced by the interactions between VP's and otherwise formulated VTA/C's) may be hardened by oxidation or with anhydrous acids such as maleic and the like. Particularly when so treated, and even though they may contain part of the VTA/C in reacted or unreacted form, such resins may be advantageously employed as fillers and binders in a variety of wood products including composts, pulps and papers, and chip and particle boards and in many other manufacturing processes. This can result in a reduction of the amount of resins, glues, and other binders required in such processes and a concomitant reduction in VP emanations from the wood product later on.

In the low concentrations in which they are present, the unreacted VTA/C constituents may even advantageously act as fillers, bleaches, or catalysts, making the reaction byproducts useful in applications in which lighter or "bleached" boards and filled resins or glues are employed. As specific examples, the treatment of collected and dried terpene resins with allotropes of oxygen, ultraviolet light, or maleic anhydride can promote oxidation reactions, providing a range of resinous or polymerized compositions which can be used as coadhesives or fillers.

Thus, in some instances, the originator of VP's may be able to use or even market resins and other products collected from VTA/C-containing spent scrubbing media—for example, as adhesives in the processing of chips and wood products and elsewhere. As another example, maleic acid adducts of terpene resins may be substituted for rosin in paper sizing, thereby gaining another practical or economic advantage from a constructive use of a byproduct generated in the resolution of a VP problem.

Facilitators and initiators may often advantageously be included in VTA/C's or made available for interaction between a VTA/C and a VP ahead of or in the reaction zone. Also, some VP streams or VP-VTA/C interaction products may already contain one or more necessary facilitators or initiators.

Facilitators for promoting VTA/C-VP reactions include free radicals, free radical initiators, photochemical sensitizers, microwave energy, oxygen allotropes, peroxides, other metal oxides, and halogens. Direct or diffused gamma rays; x-rays; and visible, infrared, and ultraviolet actinic radiation originating from natural sources such as sunlight and artificially generated actinic radiation may also be employed. The actinic energy may be generated by calcium, sodium, and mercury vapor lamps; a silent electrical or corona arc discharge; or a laser or other source of actinic light. Artificially generated ultraviolet radiation and direct sunlight are most often preferred but some VP's require otherwise provided specific—including mixed—forms of actinic radiation.

Other important facilitators which may be included as VTA/C additives or employed to furnish more effective VTA/C-VP interactions include:

Photochemical sensitizers—preferred for a wide variety of VTA/C-VP interactions are: benzoyl peroxide; benzil; benzoic acid; benzaldehyde; methylene blue; eosin; thiaxanthone; and copper, cobalt, aluminum, magnesium, hydrogen, silver, and zinc compounds.

Halogens and cohalogens alone, or combined, are in general, and depending on their form, already more-or-less photochemically potentiated. VTA/C's may nevertheless require the addition of a photochemical facilitator to provide the most efficient VP devolatization.

Photosensitization is particularly important in the stabilization of many, if not most, VP substrates and is also particularly important in the treatment of hydrocarbons. Photosensitization may be required, and has been found effective, to initiate or produce significant accelerations and increases in efficiency of some VP devolatization treatments. VTA/C interactions with saturated hydrocarbons are more readily accomplished in the presence of actinic radiation and/or heat. Unsaturated paraffins interact with VTA/C's in the presence of light and in the dark, in liquid and vapor phases, and with or without a catalyst or other reaction promoter. However, the interactions may nevertheless be speeded or made more efficient by actinic radiation or heat. Thermal and actinic radiation, especially the latter, can also materially increase the range of VTA/C-VP devolatization interactions.

Many hydrocarbons exhibit only minute ionic activity. Addition of the foregoing photochemical sensitizers increases dramatically the ionic properties of many hydrocarbons. Upon subsequent illumination, the actinic radiation effects a much wider range of devolatization reactions, especially those leading to the devolatization of hydrocarbons in general and aromatic hydrocarbons in particular. For example 6 mmoles of benzoic acid added to 30 mmoles of $CuCl_2$ in toluene increased the ion concentration of the hydrocarbon by $11 \times 10^{12}$ MHO per $cm^3$ upon subsequent illumination with actinic ultraviolet radiation at 2537 angstroms. Similar increases were noted when one or more photosensitizers were added to benzene, ethylbenzene, o-xylene, mesitylene, n-propylbenzene, and n-, sec-, and tert-butylbenzenes.

Initiators—initiate chemical reactions and are consumed during the initiation process. They are species which are either free radicals or ionic in nature. The preferred free radical initiating techniques make use of peroxides, azonitriles, photoinitiators, and high energy radiation.

Free radicals and free radical initiators enhance VTA/C treatment of many VP's containing aromatic compounds, particularly those with allyl side chains, and some saturated hydrocarbons. There are three general ways in which free radicals can be produced in the VP devolatization and substrate stabilization processes of the present invention: thermal bond homolysis, one-electron redox reactions, and irradiation processes. Many reactions between VTA/C's and VP's are promoted, initiated, or sustained by providing for one or more of these three free radical producing mechanisms.

Photoinitiators—generate free radicals via excitation by light (primarily in the ultraviolet range). The free-radical generating processes involve direct photocleavage of the photoinitiator, atom transfer from a hydrogen donor, or energy transfer to a coinitiator. High energy radiation fragments chemical bonds directly and thereby produces both free radical and ionic species. Photoinitiators are used in VTA/C-VP interactions in a manner analogous to that in which they are used in curing polymeric precursors. Among the preferred chemical initiators are organic peroxides for cationic desolublization and organolithium compounds for anionic polymerization. Lewis acids and Friedel-Crafts halides can be used to initiate cationic treatments of VP's by VTA/C's.

Free radicals can be made available in the reaction zone by providing them or their precursors in VTA/C's or by direct addition to or synthesis in the treatment zone. This can be accomplished by providing molecular oxygen, nascent oxygen, ozone, or ultraviolet or ionizing radiation to the treatment zone or by incorporating a free radical initiator in the VTA/C. Free radical initiators that can be used include: hydrazine; hydrogen peroxide; calcium peroxide; boron oxide and peroxide; iodobenzene; hydrogen magnesium sulfide; malonic acid; manganic hydroxide; methyl ethyl ketone peroxide; methyl isobutyl ketone; molybdenum carbonyl; p-methane hydroperoxide; redox initiaors such as sodium bisulf ite, sodium borohydrate, and stannic chloride; tert-alkyl hydroperoxides such as tert-butyl hydroperoxide; tert-butyl peracetate; 1-[(1,1-dimethylethyl)azo] cyclohexane carbonitrile; pentaerythritol; 2-chlorothiaxanthone; 2,4-pentanedione peroxide; 9,10-anthraquinone; and 9,10-phenanthraguinone. In many instances, the foregoing are available in the VP or VP substrate; for example, if the substrate is a pulp or paper mill effluent.

Other initiators and promoters for aiding in the production of free radicals are: n-nitrosoacetanilide, n-vinyl-2-pyrrolidinone, n-vinylcarbazole, p-methane hydroperoxide, peroxyesters, potassium peroxydisulfate, sodium borohydride, stannic chloride, tert-amyl peroctoate, tert-butyl peracetate, tert-butyl perbenzoate, tert-butyl peroxy-2-ethylhexanoate, tert-butyl peroxyneodecanoate, tert-butyl peroxypivalate, and tert-cumyl hydroperoxide.

Preferred in many cases are: hydrazine, hydrogen peroxide, hydrogen sulfide, sodium bisulfite, and pentaerythritol.

Catalysts—these are employed to promote or increase the rate of reaction between a VTA/C and a VP.

Suitable catalysts (which may also serve as photoinitiators or sensitizers) as supplied to a VTA/C-VP reaction zone to improve overall performance include: acetylcyclohexanesulfonyl peroxide; acrylonitrile; alkali metals; alpha-diethylacetophenone; alpha-dimethoxy-alpha-phenylacetophenone; aluminum trichloride; antimony pentachloride; azo initiators; azonitriles; benzoin ethers; benzophenone; boron trifluoride; carbon tetrachloride (sometimes available as an intermediate or reaction product in some VTA/C-VP reactions); carbonium ion salts; chlorination initiators; cobalt naphthenate; cumene hydroperoxide; tert-cumyl hydroperoxide; cupric sulfate; cuprous chloride; cyclohexanone peroxide; di(tert-butylperoxy)ketals; 2,4-dichlorobenzoyl; di(n-propyl) peroxydicarbonate; di(tert-butyl) diperoxyazelate; di(tert-butyl) peroxide; diacetyl peroxide; diacyl peroxides; dialkyl peroxides; dialkyl peroxydicarbonates; dibenzoyl peroxide; diacetyl peroxydicarbonate; dicumyl peroxide; oxylperoxydicarbonate; diisobutyryl peroxide; diisopropyl peroxydicarbonate; diisopropylbenzene monohydroperoxide; dilauroyl peroxide; dimethylaniline; dodecyl mercaptan; ethyl-3,3-di(tert-butylperoxy)butyrate; ferrous ammonium sulfate; diacyl peroxides; peroxyesters; peroxydicarbonates; diperoxyketals; titanium tetrachloride; triethylaluminum; xanthone; 1-[(1,1-dimethylethyl)azo]cyclohexanecarbonitro; 1-[(1,1-dimethylpropyl)azo]cyclohexanecarbonitrile; 1-phenyl-1,2-propanedione-2-o-benzoyl oxime; 1,1-azobiscyclohexanecarbonitrile; 1,1-di(tert-butylperoxy)-3,3,5-trimethylcyclohexane; 1,1-di(tert-butylperoxy) cyclohexane; 2-(tert-butylazo)-2-methylpropionitrile; 2-[(1,1-dimethylethyl)azo]2-methylbutanenitrile; 2-[(1,1-dimethylethyl)azo]2,4-dimethylpentanenitrile; 2-[(1,1-dimethylethyl)azo]4-methoxy-2,4-dimethylpentanenitrile; 2-chlorothiaxanthone; 2,2-di(tert-butylperoxy)butane; 2,2'-azobis(2-methylpropionitrile); 2,2'-azobis[2,4-dimethyl] pentanenitrile; 2,4-pentanedione peroxide; 2,5-di (benzoylperoxy)-2,5-dimethylhexane; 2,5-di(tert-butylperoxy)-2,5-dimethylhex-3-yne; 2,5-di(tert-butylperoxy)-2,5-diethylhexane; 2,5-di(2-ethylhexanoylperoxy)-2,5-dimethyhexane; 2,5-dihydroperoxy-2,5-dimethylhexane; 4,4'-bis(n,n'-dimethylamino)benzophenone; 9,10-anthraquinone; 9,10-phenanthraquinone; dialkyl peroxides; hydroperoxides; ketone peroxides; hydrogen peroxide; and peroxydisulfate salts.

Peroxide initiators generate free radicals by thermal or electron transfer (redox) processes. When high temperatures (above 100° C.) are encountered in a VP devolatization process as described herein, symmetrical and unsymmetrical azonitriles may be included to generate free radicals. These compounds are almost exclusively effective due to thermal activation, being almost inert to chemical promoters.

In many cases (frequently if the VP has a significant concentration of mixed hydrocarbons), hydroperoxide initiators or promoters are provided or generated to facilitate VTA/C-VP interactions and reduce pollution in low temperature applications. The resulting reduction of pollutants may be dramatically improved by the use of oligodynamic metals. For most low temperature applications and peroxide liberating conditions, transition metals and their salts are preferred. These are excellent VTA/C-VP interaction activators, probably due to electron transfer mechanisms. Any oxidation state of a transition metal (Fe, Mn, V, SN, Cu, Co, etc.) can be taken advantage of to decompose a hydroperoxide which, if available at a VTA/C-VP reaction zone, may support a chain of reactions. In consequence, even a small or trace amount of transition metal ion can initiate the decomposition of a large amount of hydroperoxide and consequently accelerate decomposition and simultaneously increase the velocity and efficiency of the VTA/C-VP interaction. VTA/C's containing oligodynamic transition metals (unless partitioned by ammination, antioxidants, and other means as described earlier) should not be premixed with the peroxide or initiator until just prior to or during VTA/C contact with the VP in the reaction zone or with the VP prior to contact with the VTA/C in the reaction zone, preferably in conjunction with exposure of the VTA/C and VP to actinic radiation.

It is possible for the oligodynamic metal ions in VTA/C's to destroy free radicals in the VTA/C-VP reaction zone by any one of several radical-oligodynamic metal reactions. The significance of these interactions is that the free radicals are no longer transitionally available to initiate favorable VTA/C-VP reactions in the reaction zone. It may therefore be desirable in particular applications for the level of oligodynamic metal(s) in the treatment zone to be very low.

Also, when too much oligodynamic metal is used in a VTA/C, peroxides decompose quickly. This can favor or adversely affect VP devolatization efficiency, depending on the specific VP being treated.

In most instances, it is desirable to form or generate the necessary free radicals in the reaction zone by providing facilitators which will release free radicals upon exposure to actinic radiation. However, it is also feasible to otherwise provide free radicals to enhance VTA/C-VP pollutant reduction interaction. For example, ozone, molecular and atomic oxygen, boron oxides and peroxides, and ketone peroxides may be used (primarily in normal temperature ranges) to facilitate control of unsaturated, polyester resin vapors if an oligodynamic metal compound such as an aluminum, cobalt, iron, zinc, or copper bromide or bromate or cobalt or a metal soap such as a naphthenate is present in the VTA/C. The foregoing and other peroxides contain the hydroperoxy (—OOH) grouping and, therefore, behave much like the hydroperoxides (except that they are mixtures with somewhat lower thermal stability).

Other peroxides can be similarly used to lower decomposition temperatures, usually at some sacrifice in radical efficiency. A dibenzoyl peroxide-dimethylamine (BPO-DMA) combination may advantageously be used as a facilitator in VTA/C's formulated for treating VP's comprised substantially of unsaturated polyester resin vapors. Here, the aromatic tertiary amine probably attacks the BPO to form an ion pair which decomposes to form a cation and a benzoyloxy radical which, in turn, facilitates the overall VTA/C-VP reaction.

Examples of other peroxide redox systems that may be useful for VTA/C-VP interactions are: hydrogen peroxide-ferrous ammonium sulfate; hydrogen peroxide-dodecyl mercaptan; ozone and cobaltous chloride; potassium peroxydisulfate-sodium bisulfite; potassium peroxydisulfate-dodecyl mercaptan; and potassium peroxydisulfate (or the corresponding sodium or ammonium salt) in combination with a reducing agent.

Hydrogen peroxide in combination with an oligodynamic metal (particularly a transition metal) may also be used in those applications where high water and low oil solubility is not a problem or has been overcome by a surfactant, solvent, or other coupling agent included in the particular VTA/C for that purpose.

Other systems which may be used in specific VTA/C-VP interactions where the generation of free radicals may not be practical due to inherent constituents or reaction conditions or the VP, VTA/C, or VP-VTA/C combination include: sodium borohydrate; molybdenum carbonyl and carbon tetrachloride; malonic acid and a trivalent manganese compound; triethylaluminum and cuprous chloride; manganic hydroxide and hydrazine; cupric sulfate and hydrazine; a n-alkylhydroxylamine and trivalent titanium; copper complexes and carbon tetrachloride; transition metals and organic halides; diazonium salts and transition metals; aralkyl halides and silver; iodobenzene and magnesium; n-nitrosohydroxylamines; n-nitrosoacetanilide; and certain hexasubstituted ethanes. Of these free radical generating systems only a few—those underlined and those which are at least in part inherently provided by the VP or as a result of combining a given VP and VTA/C)—are, where available, preferred over directly added peroxides or azo initiators.

No facilitator is necessarily required for the VTA/C treatment of more reactive aromatic VP's such as phenol. For example, a VTA/C comprised entirely of a halogen and a cohalogen such as bromine and chlorine, usually in an equimolar ratio, is quite effective for treating pollutants comprised of phenols and comparable VP's.

Radical-induced decompositions of peroxides result in inefficiency in radical production since the peroxide decomposes without adding more radicals to the system. Such decompositions generally occur when the VP's contain substantial concentrations of olefinic substances as these substances scavenge the initially generated radicals.

In nonscavenging (e.g., nonolefinic) environments, induced decomposition probably occurs with peroxides that are labile and is more pronounced as the concentration is increased. The homolysis of organic peroxides is a first-order reaction whereas the radical-induced decomposition is a second-order reaction. Therefore, decomposition rates are significantly faster than the true first-order rates in those peroxide systems where induced decomposition is also occurring. Most peroxides decompose faster in more polar or polarizable environments. This is true even if the peroxide is not generally susceptible to radical-induced decomposition.

Adjuncts are employed in the VTA/C's disclosed herein for their surfactant, solvent, and/or carrier capabilities to improve or extend contact or interaction between VTA/C's and VP'S. Useful adjuncts include: water; acetic and other lower alkyl acids and solutions of their salts; mineral acids such as sulfuric, hydrochloric, and phosphoric; conventional surfactants and solvents; aprotic solvents such as dimethylformamide, benzene, methylene chloride, hexamethylphosphoric triamide, 1-methyl-2-pyrrolidinone, and dimethyl sulfoxide; polyols; ethers; chloroform; carbon tetrachloride; tetrachloroethane; ethylene bromide; nitrobenzene; sulfuryl chloride; aqueous and alcoholic solutions of hydrochloric, hydrobromic, and alkali bromides; halogen and halide vapors in carbon dioxide; nitrogen; methanol; ethanol; propanols and butanols; methylene chloride; dimethyl phtalate; and pyridine. Also, at times, a VP being treated or another functional component of the VTA/C such as a halogen or cohalogen can perform the function of the facilitator. By class, preferred facilitators for the treatments of hydrocarbons include:

Alcohols:
 Preferred: monohydric
 Most preferred: methanol, ethanol, n-propanol, isopropanol
Ethers:
 Preferred: aliphatic including glycol ethers
Heterocyclic Compounds:
 Preferred: pyridine
Aprotic (proton neutral) solvents:
 Preferred: dimethylsulfoxide As suggested above, simple but effective and important VTA/C's are those (preferably photosensitized) comprised of bromine or chlorine and an oligodynamic metal or a cohalogen or sources of those constituents. Typically, the best results can be achieved by reacting the VP to be treated with a VTA/C of this character in a zone exposed to actinic radiation such as that in the visible or ultraviolet portion of the electromagnetic spectrum. Para-chlorophenylmagnesium bromide is particularly photosensitive in the presence of oxygen as are many alkyl Grignard reagents, any of which may be used to good effect in VTA/C's. Surfactant/solvent adjuncts can also often be employed to advantage in promoting the effectiveness of these simple VTA/C's.

Olefins are among the VP's that are particularly susceptible to treatment with even simple VTA/C's. The reactions between bromine and olefins are rapid; and the treatment has the advantage that VTA/C's containing bromine produce in the devolatization of olefins bromine-saturated olefins that can more readily be subjected to VTA/C pollutant control by devolatization; for example, by capture in VTA/C scrubber media.

Decomposition rate studies on hydroperoxides for VTA/C formulation and with respect to the solvent activity inherent in some VP's upon treatment show dramatic solvent effects which primarily result from their susceptibility to induced decomposition. In decreasing order of stability: trichloroethane>saturated hydrocarbons>benzene>alcohols. Many of these solvents are encountered in VP's or as intermediates once treatment between a VTA/C and a VP has been initiated. Decomposition rates are slowest in trichloroethylene, most probably because it is a radical scavenger and thereby prevents radical-induced decomposition. Trihalogenenated hydrocarbons resulting from VTA/C-VP interaction provide a unique degree of stability to hydroperoxides and other initiators of free radicals.

Contrary to expectation and to what has heretofore been taught, bromine appears to be more reactive than chlorine in the treatment of many VP'S. For example, bromine-containing VTA/C's react readily with such diverse VP pollutants as carbon monoxide, carbon dioxide, xylene, styrene, asphalt tars, coal tars, and cumene, especially when the reaction is promoted by thermal energy, actinic radiation, or another of the facilitators identified above. At least in the treatment of hydrocarbons, this is certainly inconsistent with the widespread belief that chlorine is the superior, not inferior, "oxidant".

Because it is much more efficient in devolatizing VP's, bromine is also significantly more cost effective than chlorine.

VTA/C'S for treating VP's released from biological substrates and employing bromine as a primary halogen without a cohalogen also preferably have at least a surfactant and/or a solvent to: (a) improve contact between the VTA/C and the VP's being treated, and (b) enhance reaction efficiencies although bromine by itself is frequently adequate for many hydrocarbons. The addition of selected adjuncts such as acetic acid, pyridine, ethanol, methanol,and the like—usually in small concentrations (below about 1%)—can measurably improve the overall performance of a bromine-based VTA/C and is also preferable when bromine is employed in combination with chlorine.

The most preferred VTA/C's for the broadest applications and highest efficiency of VP reduction employ a primary halogen, preferably bromine, and at least one cohalogen in combination with an oligodynamic metal or metal complex (preferably magnesium, aluminum, and/or cobalt) and at least one surfactant/solvent adjunct which is typically selected to promote devolatization reactions between the VTA/C and the predominant specie(s) in the VP being treated. In other cases, the adjunct may be selected to promote interactions which would otherwise not readily occur (if at all), irrespective of whether or not a targeted specie is a dominant one.

If the VTA/C contains both bromine and chlorine, alkenes may, at least in part, be effectively devolatized (even if only intermediately) to bromochloro compounds; and some hydrogen may be replaced by bromine, yielding an organic bromide and hydrogen chloride. VTA/C reactions that involve the replacement of hydrogen by bromine as might be the case with saturated hydrocarbon VP's such as alkanes and alkyl aromatic compounds is promoted by free radical chain reactions and requires free radical, thermal, photolytic, or other initiation. An example is a VTA/C containing hydrobromic acid, aqueous acetic acid, and a small amount of sodium acetate for treating carbon tetrachloride, a halocarbon VP.

As a rule, the gas streams containing more complex combinations of VP'S and volatiles with more complex molecular structures, particularly heterocyclics, are more difficult to treat. Available treating equipment and conditions at the treatment zone which may already be existent can add to the difficulty of effective volatile reductions by VTA/C treatment. Generally, the more difficult the VP's are to treat, whether due to operating conditions, equipment limitations, complex volatile profiles, molecular stability of pollutant components, or other reasons, the larger the number and the higher the concentration of the VTA/C constituents discussed above that will usually be required to provide a VTA/C treatment capable of accomplishing effective devolatization.

In short, treatments requiring more effective removal of a wider variety of VP's than is normally possible with a VTA/C containing only bromine or a VTA/C comprised of chlorine or bromine with a cohalogen may sometimes entail the use of one or more other reaction-promoting constituents.

The selection of VTA/C components is frequently a complex issue and dependent upon the complexity of the VP or VP complexes to be treated, practical conditions encountered in treating, substrates (if any) requiring stabilization, and the objective of the treatment. Specific selections vary with each specific volatile complex, other conditions, and treatment objectives but may be readily determined by empirical selection and VTA/C-dose-volatile reduction response. Major treatment enhancements may be obtained by testing volatile substrates under conditions as similar to actual as possible against a series of VTA/C's.

The VTA/C should be formulated to substantially devolatize the VP or VP's being treated by conversion of the offending substance(s) into liquids or solids or to so alter the solubility of the treated VP or VP's as to optimize removal of the pollutant from the ambient air, liquid stream, or other environment in which it is found. In each instance this facilitates entrapment and collection of the VTA/C treated VP or VP's.

Candidate VTA/C's are preferably formulated as follows: add halogen (preferably bromine or chlorine or a source thereof) starting at 0.05% in equal incremental concentrations to the VTA/C carrier constituent to obtain the best measurable effect. Then, add to the carrier/halogen mix in any order but preferably in the listed order until the best measurable effect in terms of VP devolatization is obtained:

cohalogen(s);
oligodynamic metal(s);
adjunct(s);
facilitator(s) (if employed, provide actinic light last).

The cohalogen and oligodynamic metal constituents may be supplied in elemental form if conditions permit, or any appropriate sources of those VTA/C components may be employed.

Chlorine and other halogens may of course be used as the primary halogen in this formulation protocol instead of bromine. These substitutions do, however, require that at least one of the following be employed: a cohalogen; an oligodynamic metal; a facilitator; or an adjunct with solvent and/or surfactant properties vis-a-vis the VTA/C and the VP.

Highly efficient VTA/C's effective against the widest combinations and most intransigent varieties of volatile pollutants including saturated and unsaturated hydrocarbons such as paraffins, terpenes, olefins, benzenes, and many others may be obtained by combining a halogen, a cohalogen, an oligodynamic metal, and an adjunct and using a facilitator which may involve exposing the reaction zone to actinic radiation.

As discussed above, an empirical approach to the formulation of a VTA/C is generally preferred, if not essential. Within this stricture, there nevertheless are limits on the relative proportions of VTA/C constituents, particularly those major ones discussed above. These in most cases are:

Ratio of VTA/C to VP:
- Operable: from 0.00001% to 300% of VP
- Preferred: from 0.05% to 20% of VP Ratio of primary halogen to cohalogen:
- Operable: from 9999:1 to 1:1 parts by weight, based on the total weight of the VTA/C
- Preferred: from 9:1 to 1:1 parts by weight, based on the total weight of the VTA/C Oligodynamical metal (weight percent based on the total weight of the VTA/C)
- Operable: from 0.001 to 99
- Preferred: from 0.1 to 50

Adjunct (same weight percent basis)
- Operable: from 0.01 to 99
- Preferred: from 1 to 10

Facilitator (same weight percent basis)
- Operable: from 0.01 to 99
- Preferred: from 1 to 10

The concentration of cohalogen in the treatment agent when bromine, fluorine, or iodine is the primary halogen may range from zero percent (no cohalogen) to 50 percent (a treatment agent containing only a primary halogen and a cohalogen and the maximum ratio of cohalogen to primary halogen).

Conventional buffers, acidifiers, alkalizers, catalysts, and other constituents needed under specific conditions of treatment and for some VP's may be added to the VTA/C as required.

As was pointed out above, the use of bromine as opposed to chlorine for treating VP'S—particularly those which are comprised of or derived from aliphatic and cyclic compounds—contrary to expectation yields immediate and effective results. Chlorine alone, even in high concentrations, is mostly or wholly ineffective against VP's such as terpenes, styrenes, crude petroleum, and asphalt tars to mention only a few examples. However, when chlorine is replaced by or supplemented with a cohalogen or source thereof such as bromine; an oligodynamic metal; actinic light; or a combination of the foregoing in addition to either a facilitator or adjunct, even in extremely low concentrations, effectiveness is profoundly improved.

The marked improvement noted upon replacement of chlorine with bromine is even more surprisingly amplified, both in diversity and intensity of the reactions that are effected, when bromine, chlorine, and other halogens are used in conjunction with each other in a primary halogen/cohalogen relationship. This is also noted when iodine or fluorine or sources of those halogens are used as cohalogens. This makes possible the significant reduction of VP's heretofore substantially unamenable to conventional treatments.

The selected VTA/C can be injected directly into the stream or body being treated; it can be employed in a packed bed or with a filter; it can be injected into an effluent line; or it can be used in a scrubber. A countercurrent or reverse flow jet scrubber is effective and for economic and trouble-free operation is suitable, especially if the treatment chamber contains provisions for application to the devolatization reaction zone of actinic light.

Alternatively, the VTA/C may be sprayed upon or added as an aerosol, dust, or powder to substrates which evolve VP's such as: composts; municipal wastes; or the impregnated wood shavings, chips, or sawdust used for forming particle and chip boards.

Another effective way of implementing the present invention is to impregnate a porous, activated carbon such as activated charcoal or a zeolite with the VTA/C. Activated charcoal and zeolites adsorb a VTA/C containing a primary halogen such as bromine or a cohalogen reversibly without reaction when moisture is absent. In the presence of moisture, the carbon or zeolite is partially oxidized; and, in the exemplary case of bromine and carbon, hydrobromic acid, a source of VP-controlling bromine, is formed and released to the VP-VTA/C interaction site.

With few exceptions, it is important that water or water vapor be present in the reaction zone to ionize the VTA/C. In many cases, this water may be driven off and made available to the VTA/C in the course of a manufacturing process. In other circumstances, the water must be otherwise supplied. Specifically, VP's may be driven off in manufacturing steps carried out at temperatures as low as 20–40° C. At these low temperatures, water may not come off the materials being processed fast enough to make it available in the quantities needed for the VP-devolatizing reactions to proceed efficiently. In that case, water must be supplied to the reaction zone —separately or as the carrier component of the VP; or the very small ionic potential of the hydrocarbons in the VP must be raised—for example, by making benzil or copper ions available.

Particularly in applications where VP's are present in a process effluent, they may be effectively treated in a contact scrubber system. In this case, the selected VTA/C may be distributed in a gaseous or aqueous carrier at a concentration between about 0.001 percent and 200 percent by weight of the VP's to be treated. The ratio of other constituents to carrier will typically be in the range of 0.01 to 50 percent.

Concentrations and treatment efficiencies depend on the efficiency of contact and contact means such as an aerosol or scrubber, the concentration of the VP's in the effluent, the temperature in the reaction zone, flow volumes, the velocity of effluent and media on impaction or contact, and other situational variables. A typical preferred starting concentration of VTA/C in a representative example involving 500 cfm of effluent with a VP concentration of 350 ppm is 25 gallons per minute of water containing 2.5 lbs of the VTA/C. Instrumentation monitoring of the effluent before and after treatment will indicate the need for more (or less) VTA/C which may be added or subtracted in convenient increments to determine optimal responses.

In many applications, the spent scrubbing media contains VTA/C-complexed VP's such as, for example, when the VP's are styrene-, terpene-, terpenoid-, or fatty acid-based. In these instances, settling, centrifugal force, filters, floccing agents, distillation, or additives such as appropriate copolymers, cross-linked compounds, oxidizers, and reaction promoters (including, for example, ultraviolet light, molecular oxygen, ozone, atomic oxygen, hydrogen peroxide, free radicals, acids, and excess water) may be used to cleanse or rejuvenate the scrubbing media. Here, again, an empirical approach can be employed to produce the most efficacious method for recovering complexed volatiles, particularly those which may be of some inherent or potential value, and for restoring the activity of all or part of the scrubbing media. Primary considerations are: best constructive use vs. least costly treatment of any given spent media vs. the value of potentially recoverable reaction products.

For example, scrubbing media burdened with terpene resins may be formed during effluent treatment by contact at about the same pH as the effluent. It is undesirable to attempt to avoid the formation of these resins. This may result in blocking the catalytic activity of the bromine- and/or chlorine-containing VTA/C and reducing its efficiency in removing contaminants from the effluent stream. To regenerate spent contacting medium contaminated with terpene or styrene resins, the contaminated contact medium may be treated with water and a dilute mineral acid such as nitric or sulfuric or a weak acid such as acetic.

In other applications, known techniques may be used to recover the halogen(s) from the VTA/C-VP interaction products. These techniques include:

1) recovery for use in situ or elsewhere by employing an oxidizing agent (e.g., hydrogen peroxide, sodium bromate, chlorine, [O], $O_2$, or $O_3$) to convert evolved HBr to bromine which is then consumed by the reaction; and
2) the use of an alcohol to coproduce an alkyl bromide by the reaction of the byproduct HBr with the alcohol. Methanol is the alcohol of choice.

In some applications, such as those involving waste water from pulp or paper processing, VTA/C's may be added directly to the waste water substrate or holding tank head space, as well as directly to process offgases. This dual treatment approach makes up for difficulties in offgas treatment which may be experienced due to lack of control over the wastes.

In general, the VTA/C should be reacted at a pH other than neutral. An acid pH is usually effective if the VTA/C contains at least a halogen/cohalogen/oligodynamic metal combination of constituents and actinic light is present during the reaction phase. However, VTA/C's containing alkaline ingredients or buffers—for example, amines, detergents, surfactants, sodium and potassium hydroxides, and sodium silicates—have proven equally effective in treating many VP's and VP-releasing substrates.

It is thus a feature of the present invention that the pH in the reaction zone can vary over a wide range from very low to very high, depending to a great extent upon the inherent pH of the VP's in the process effluent and the particular effluent-to-VTA/C interaction characteristics. This is a particularly important advantage because the relative pH of any given volatile effluent may vary over a wide range. For example, fatty acid and fatty acid-dominated effluents will almost always have an acidic pH. On the other hand, terpenes and terpenoids may appear in effluents exhibiting a wider range of pH's.

If the effluent stream over time causes the pH in the reaction zone to shift into a range where the selected VTA/C becomes ineffective, or if the pH is initially at a level at which the efficiency of the separation process is less than optimum, buffering of the scrubbing composition may be necessary. For example, a pH of about 4.5 has been found effective in scrubbing terpenes from air streams contaminated with those compounds; and lower or higher pH's do not appear to substantially improve VP devolatization. The hydrolysis of methyl bromide to methanol and hydrobromic acid proceeds very slowly in aqueous solution but more rapidly in dilute alkalies.

A number of buffers that can be used for pH adjustment were identified above. These include dilute mineral acids; organic acids; bases; and salts such as acetates, borates, phosphates, and phthalates. Among the mineral acids that can be employed are nitric, sulfuric, and hydrobromic. Hydrochloric acid is sometimes avoided as it appears to interfere somewhat with the activity of some VTA/C's which can otherwise be effectively used to treat hydrocarbons.

Maintenance of an appropriate reaction zone pH can be particularly important in those applications of the invention in which a substrate containing sulfur compounds is treated with a VTA/C in which bromine is present. Under alkaline conditions, the VTA/C bromine can react with available sulfur to form mercaptans and thioethers. As byproducts of VTA/C-substrate interactions, these substances are highly undesirable. Thus, in this case, it is appropriate to adjust the reaction zone pH to a non-alkaline level or to use a VTA/C containing aluminum, zinc, magnesium, or boron.

The just-discussed problem does not appear, and there may be advantages whether or not the reaction zone pH is alkaline, if the substrate contains methyl or amino compounds. A substrate containing methyl compounds which is treated with a VTA/C containing bromine can release methyl bromide, and this substrate-generated bromide can be used as a bromine source for a VTA/C employed to treat other VP's released from the substrate. For example, if the substrate effluent contains amines, the methyl bromide may react with the effluent to form methylammonium bromide derivatives from which the bromine can later be removed by hydrolysis.

The reaction zone temperature may range from ambient to the maximum at which the water in the reaction zone will remain liquid and capable of ionizing the selected VTA/C at the pressure in the reaction zone. Typically, the reaction temperature will be governed by equilibrium between the VTA/C and the VP's being devolatized, the physical treatment system, and the effluent stream being treated.

A wetting agent, solvent, or detergent can often be gainfully employed to improve contact between the VTA/C and the VP's in a polluted effluent. A solvent or wetting agent is generally employed when the VP-containing effluent includes a significant concentration of aliphatic or cyclic hydrocarbons.

The wetting agent can be a detergent. Preferred are those interactions providing the best ionic potential between the VTA/C and the VP or VP substrate. Suitable detergents or surfactants include the entire range of anionic, cationic, nonionic, and amphoteric types as the situation dictates. Those surfactants containing halogen moieties such as quaternary haloammoniums, of which benzalkonium chloride is a good example, as well as iodized or fluorinated surfactants can be used to particular advantage. In this case, the halogen present in the surfactant may serve as a primary halogen or a cohalogen, meaning that the surfactant can serve in a dual capacity.

This is also true of surfactants with sulfur moieties. Such surfactants can provide catalytically active sulfur radicals to VTA/C-VP interactions, particularly if a peroxide or peroxide precursor is generated or otherwise provided in the treatment zone.

Generally speaking, if an adjunct is employed, a wetting agent or detergent will be suitable for use in devolatizing VP's of biological origin while solvents, including aprotic ones, may be required for treating hydrocarbon VP's.

Aliphatic hydrocarbons are amenable to treatment by VTA/C's containing a wider variety and combination of wetting agents or solvented VTA/C's than are the usually more resistant cyclic hydrocarbons. However, due to the often very complex and differing nature of volatile-bearing effluents (even from similar sources), wetting agent and solvent selection for a given effluent remains somewhat empirical, those detergents, wetting agents, or solvents demonstrating the best overall effect in testing usually being selected.

Good starting point solvents for VP-VTA/C interactions are carboxylic acids such as acetic, alcohols such as ethanol, ether glycols, and pyridine. Other of the solvents identified and discussed above may also be used. Required additions are customarily though not always small. Usually, an addition of less than about 1% of the VTA/C carrier will demonstrate a worthwhile improvement in VP reduction.

It may be important to employ a defoaming agent or device to prevent foam build-up from the detergent if one is used. Any of the conventional, commercially available foaming agents can be employed. These include: 2-octanol, sulfonated oils, organic phosphates, silicone fluids, stearates, and dimethylpolysiloxanes.

Indicator dyes for visually gauging the condition or degree of activity of the scrubbing media can often be incorporated to advantage in the VTA/C. This is particularly true when the dye is also a photoactivator which influences more effective pollution reducing interactions between VP's and VTA/CS. Representative examples of those dyes which may be used for this purpose are fluoresene, azo dyes, and methylene blue.

The principles of the present invention can be employed, in many cases, to make currently available pollutant treatment systems and techniques more effective. Augmentation of a conventional treating agent such as chlorine, chlorine dioxide, sodium or potassium hydroxide, potassium permanganate, or hydrogen peroxide, for example, with only small concentrations of bromine (usually less than 1%) can dramatically increase the effectiveness of the pollutant treatment.

The addition to conventional treatment systems of other major VTA/C constituents in combination with bromine—cohalogens, oligodynamic metals, adjuncts, photosensitizers, facilitators, and their sources—and exposure of the reaction zone to actinic radiation can produce unparalleled and unexpectedly efficient air purification and other pollutant reduction in existing facilities. Other advantages given existing installations by the VTA/C approach of the present invention include a broadening of the types of pollutants which can be effectively treated and more consistent results. Such augmentations can readily be made in existing facilities, making it possible to take advantage of the present invention without any substantial investment in new facilities or equipment.

Thus, the present invention provides effective approaches and techniques both for creating new pollutant control systems and for augmenting traditional systems by supplementation of existing treatment agents. For many new types of pollutant control, augmented traditional systems will prove to be of considerable effectiveness; in some cases, the systems and treating agents will necessarily be primarily or solely of the VTA/C type.

Those tests described in the examples which follow were conducted on a variety of hydrocarbon-based VP's and on VP's evolved from biological matter. The treatment agent (VTA/C) as well as the material to be treated was varied. Favorable efficiencies in the reduction of the offending VP's were consistently obtained.

EXAMPLE I

Two hundred (200) cfm of an air influent at 40° C. containing phenol, cresol, xylene, and acetone totalling 350 ppm as measured by a flame ionization detector was employed as the test, VP-containing gas.

A VTA/C (No. 1) was used as the treating media. VTA/C No. 1 contained 1% hydrobromic acid (42% concentration), 0.20% of an 8% chlorine solution, 0.20% of aluminum or zinc chloride or bromide, and 0.25% alcohol. The balance of VTA/C No. 1 was water.

Fifty (50) gallons of the VTA/C was applied through a reverse jet nozzle in a 4"×30" column. The rate of application was 20 gpm. The treatment zone (VTA/C contact with incoming gas) was bathed with actinic radiation generated by a 68 watt mercury vapor light outputting ultraviolet energy in the wavelength range of about 4050 Å to 6000 Å.

VP reduction results were measured by a flame ionization detector in ppm of mixed volatiles.

The following results were obtained:

| | VP concentration (ppm) |
|---|---|
| Initial | 350 |
| VTA/C Flowing, UV Light Off | 70 |
| VTA/C Flowing, UV Light On | 27 |
| Addition of $O_2$ to the Reaction Zone (8 liters per minute) with the UV Light On | 12 |
| Addition of $O_3$ to the Reaction Zone (8 liters per minute) with the UV Light On | 6 |

The test was repeated, employing a VTA/C containing 95 percent water and 5 percent aluminum bromide and air contaminated with phenol vapors. The results of this test follow.

| | Phenol Concentration (ppm) |
|---|---|
| Initial | 225 |
| VTA/C Only | 140 |
| VTA/C plus UV Light (2357Å) and Oxygen | 15 |

Also treated in the manner just described were air streams contaminated with: bisphenol, xylenol, resorcinol, naphthol, phenolic resins, epoxy resins, and pentachlorophenol. Reductions of the air stream contaminant ranging from 50 to 98% were obtained in each case.

Alkenes in general prove easily amenable to treatment with VTA/C's. The VTA/C treatment of phenol, for example, takes place rapidly even with quite dilute aqueous solutions of the active constituents. Iodine as a cohalogen seems to speed this treatment. on the other hand, the interaction proceeds more efficiently in terms of total reduction when aluminum bromide is a VTA/C component and when treatment takes place at higher temperatures or under pressure.

Another approach is VTA/C treatment in the presence of heat and a reaction promoter such as ferric bromide. Also effective is VTA/C treatment under ultraviolet radiation or at a higher temperature with a catalyst. After a short initial reaction time, the VTA/C treatment process becomes more rapid.

Different VTA/C's demonstrated effective reduction of aromatic VP's having hydrogen in ortho and para positions relative to a polar group. They were less effective against nonpolar aromatic compounds and still less effective against aliphatic hydrocarbons. To improve overall effectiveness in these circumstances, the use of adjuncts and facilitators to augment VTA/C performance becomes important.

EXAMPLE II

The equipment and test procedures described in EXAMPLE I were employed. The influent was 200 cfm of ambient temperature air (35° C.) contaminated with ethylene, propane, and methane (total of 290 ppm).

The VTA/C or treating media/scrubbing bath (No. 2) was comprised of allyl chloride, 0.25%; ethyl alcohol, 0.25%; 50 ppm $O_2$, 98.5% purity at 8 liters per minute; and 0.20% hydrogen bromide.

Results:

|  | Contaminant Concentration (ppm) |
|---|---|
| Initial | 290 |
| VTA/C Only | 120 |
| VTA/C No. 2 Augmented With Benzoyl Peroxide, 0.001% | 90 |
| VTA/C No. 2 With Benzoyl Peroxide and Actinic Radiation From A Halogen Bulb | 25 |
| VTA/C No. 2 With Benzoyl Peroxide and Cobaltous Chloride, 0.01% and the Halogen Light On | 10 |

EXAMPLE III

The EXAMPLE I equipment and test procedure were employed. The influent was ambient temperature air (100 cfm) contaminated with 280 ppm of diphenyl oxide.

The scrubbing media (VTA/C No. 3) contained:

|  |  |
|---|---|
| Water | 88% |
| Hydrobromic acid | 10% |
| Lewis acid ($AlCl_3$) | 2% |
| Total | 100% |

A diphenyl oxide reduction from 280 ppm to 80 ppm was noted. Exposing the treatment zone to actinic radiation from a mercury vapor arc light resulted in an immediate additional reduction of the diphenyl oxide concentration to about 20 ppm.

One percent (1%) of bromine trifluoride was substituted for the hydrobromic acid in VTA/C No. 3. This resulted in a reduction of the diphenyl oxide from 280 ppm to 50 ppm.

$AlBr_3$ was substituted for $AlCl_3$ in the initial VTA/C No. 3 formula. The result was a diphenyl oxide reduction from 280 ppm to 65 ppm.

In companion tests, other contaminants were substituted for diphenyl oxide. The initial VTA/C No. 3 formula was employed, and the light source was varied to determine if the type of actinic light changed the effectiveness of the VTA/C.

The contaminants were present in a concentration of about 200 ppm.

Contaminant reductions were: (1) without light, between 75 and 90%; (2) with light, from 85 to 99%.

Open sunlight was about equally effective against butylbenzene, toluene, cymene, and diphenyl.

When $AlBr_3$ was employed instead of $AlCl_3$ in VTA/C No. 3, the VTA/C with 500 watts of sodium vapor light in the reaction zone was effective against xylene and cumene.

Naphthalene reduction was increased 15% by using long wave UV radiation (from about 4,000 Å to 6,000 Å). Anthracene content was reduced an additional 10% by intermittent or diffused light. Stilbene concentration was reduced an additional 8% by polarized light.

With ethanol (1%) added to the initial VTA/C No. 3 formulation, xylene, cumene, and diphenyl concentrations were reduced an additional 5 to 9% when treated with the VTA/C.

EXAMPLE IV

Referring now to FIG. 1 of the drawing, approximately 50 pounds of green wood shavings 18 taken from production lots prior to production kilning were enclosed in a 10-gallon fiber drum 20 with a removable top 22. A conventional 1500 watt hair dryer 24 was installed through a puncture 25 at the base of drum 20 just above the bottom metal retaining ring 26. The hair dryer was fixed in place by a fitting 28 surrounding the dryer nozzle 30 and installed through a smaller hole cut into the drum base. On the side of drum 20 opposite the side at which hair dryer was affixed and at a higher level, a small puncture was made. A steel tube 32 of approximately ⅜ inch inside diameter by 8 inch in length was installed in the drum through the puncture. The puncture hole was smaller than the tube, and the tube was pressure forced through the puncture and then taped into place with duct tape (not shown) to minimize leakage.

A very small hole was punched through the top 22 of the drum. A stem thermometer 34 with one-tenth degree graduations and a top temperature of 250° F. was forced into the drum through this hole.

To the end of steel tube 32 outside drum 20 was affixed a 3 foot length 36 of 9/16 inch Teflon tubing. This tubing was attached to a ⅜ inch I.D. glass tube 38 inserted through the composition top or lid 40 of a standard Waring blender or homogenizer 42. Tube 38 extended downward about six inches to a level about 1 inch above homogenizer blades 44 with the lid 40 in place. With the blender motor 46 running, this arrangement caused effluent air originating in fiber drum 20 to flow out of the drum through steel outlet tube 32 and through the Teflon tubing 36 and glass inlet tube 38 to within 1 inch of the homogenizer blades 44.

Five hundred mls of an aqueous scrubbing medium 48 VTA/C No. 4) was prepared and poured into blender 42. This filled the blender to about half of its effective capacity.

A second tube 50 of the same diameter as inlet tube 38 was inserted through the blender cover 40 on the opposite side of the cover from the glass inlet tube. This tube was about 4 inches in length. It was so installed that about 2.5 in of the tube projected from the blender cover 40 when the cover was affixed to blender 42. The tube extended about 1.5 in inside the cover. Tube 50 served as an exhaust for effluent air derived from the shavings 18 in fiber drum 20 after the effluent had been scrubbed with the treatment agent 48 (VTA/C No. 4) by directing the effluent across blender blades 44 via inlet tube 38.

A hand-operated, three-way glass valve 52 was fixed by a Teflon tube 54 to blender exhaust tube 50. Rotating the valve through the three possible positions would: (1) shut off the blender exhaust, (2) direct the exhaust to the plenum of an IR scanner 56 (a Wilkes Miran IA gas analyzer) through tubing 57, or (3) discharge the effluent to the ambient surroundings through valve port 58. This port could be sniffed to determine changes in the intensity or character of VP's in gases discharged from the blender.

The IR scanner 56 was set at an analytical wavelength of 3.4 m. This corresponds to primary spikes of α-pinene and l-limonene. The IR unit was also set to transmit 98 percent of the infrared energy output from its source over a path length of 20.25 m through a sample filtered through a zero filter.

The hair dryer 24 discharging into the fiber drum 20 was turned on to medium heat at full force. This corresponded on a flow meter to a flow rate of about 11 liters of air per minute.

The hair dryer 24 was operated for 15 minutes at medium heat to allow the shavings in drum 20 to come up to a minimum temperature of 100° F. as shown by the indwelling thermometer 34. VP-containing effluent was then discharged from the drum 20 through blender 42 without scrubbing into IR scanner 56. This caused an almost immediate response; i.e., an almost immediate display of spikes characterizing α-pinene and l-limonene. The response dropped over a period of minutes until an absorption of approximately 55 percent of the IR transmission was achieved. This response corresponded to 585 ppm of α-pinene and l-limonene being present in the plenum 60 of the IR scanner. The maximum absorption baseline value remained stable over a period of 10 minutes.

The homogenizer or blender 42 was then turned on to the lowest speed setting (approximately 11,000 RPM). VTA/C No. 4 in the form of aqueous scrubbing medium 48 was introduced into the blender 42 in the manner described above; and incoming effluent was directed into the scrubbing medium across the homogenizer blades 44.

The response was immediate, and the transmission of infrared energy at the 3.4 m wavelength increased rapidly over a period of about five minutes. Baseline transmission of the infrared radiation was restored to 97.5 percent of the original transmission level and, after calculating for the pressure drop through the blender, was about 99.2 percent to 99.7 percent of the original transmission level.

Sniffing the exhaust from three-way valve port 58 upstream from the IR scanner 56 resulted in a detection of contaminants which was more-or-less in agreement with the instrumentation. The range of reductions was from about 60% to 99% as indicated with each specific test. For about 97% and higher reductions, sniffing indicated that an essentially 100 percent reduction in the VP's had been obtained. This was indicative of α-pinene and l-limonene being essentially completely eliminated by reaction with the scrubbing medium. Repeated olfactory checks by numerous personnel consistently resulted in no aromatic perception of VP's.

VTA/C No. 4 was formulated as follows (initial formulation):

| | |
|---|---|
| Water | 98% |
| Zinc bromide | 1% |
| Ethyl alcohol | 1% |
| Total | 100% |

Contaminant reductions of from about 325 ppm to 130 ppm were obtained.

Aluminum bromide was substituted for zinc bromide in the foregoing formula. A reduction of terpenes from 325 ppm to 120 ppm resulted from this modification.

EXAMPLE V

Tests employing the FIG. 1 system, the procedure described in that example, and the same VP's (325 ppm) were repeated using a conventional treatment agent or scrubbing medium formulated as follows:

| | |
|---|---|
| Water | 95% |
| Chlorine 8% | 5% |
| Total | 100% |

There was no reduction in the 325 ppm concentration of the VP's.

The aqueous chlorine treatment agent was then modified by adding constituents which converted it to VTA/C's employing the principles of the present invention with the following results:

| | Modification | Reduction in VP Concentration |
|---|---|---|
| 1. | Substitution of bromine in the form of 42% hydrobromic acid for one-half of the chlorine | From 325 ppm to 120 ppm |
| 2. | Modification 1 plus the addition of 1% AlBr$_3$ | From 325 ppm to 120 ppm |
| 3. | Modification 1 or modification 2 plus the addition of 1% ethyl alcohol | From 325 ppm to 70 ppm |
| 4. | Exposure of the reaction zone to natural sunlight | An additional 50% |
| 5. | Exposure of the reaction zone to actinic radiation emanating from a halogen bulb | An additional 50% |

EXAMPLE VI

Chips dried to eliminate VP's were employed as substrates in other tests of VP reduction processes employing the principles of the present invention. The chips were placed in the drum 20 of the FIG. 1 system. The selected VP was then sprayed onto the chips, and the drum was sealed with lid 22.

The VTA/C used in this series of tests was No. 6. It was formulated as follows:

| Carrier (water) | 96.85% |
|---|---|
| Solvents | |
| alcohol | 0.45% |
| pyridine | 0.20% |
| Ferrous bromide | 0.50% |
| Bromine and chlorine | 2.00% |
| as 1-bromo-3-chloro-5, 5-dimethylhydantoin | |
| Total | 100.00% |

UV actinic light was provided at 2537 Å from a 68 watt source operating at 120 volts.

| | VP Concentration as Determined by Scanning IR, FID, and Sniffing Initial VP Concentration (ppm) |
|---|---|
| Asphalt Tars | 260 |
| Crude Petroleum | 220 |
| Kerosene | 350 |
| Naphtha | 290 |
| Gasoline | 120 |

| | VP Concentration After Treatment with VTA/C (ppm) |
|---|---|
| Asphalt Tars | 65 |
| Crude Petroleum | 50 |
| Kerosene | 30 |
| Naphtha | 25 |
| Gasoline | 30 |

| | VP Concentration After Treatment With The Reaction Zone Exposed to the Actinic Radiation (ppm) |
|---|---|
| Asphalt Tars | 35 |
| Crude Petroleum | 10 |
| Kerosene | 45 |
| Naphtha | 35 |
| Gasoline | 10 |

| | Odor After Treatment With The Reaction Zone Exposed To Actinic Radiation |
|---|---|
| Asphalt Tars | mild |
| Crude Petroleum | mild |
| Kerosene | mild |
| Naphtha | mild |
| Gasoline | mild |

Halides of aluminum, zinc, copper, and cobalt were also evaluated. They had approximately the same effectiveness as the ferrous bromide.

A combination of oxygen and actinic UV radiation was about 50% more effective than the UV radiation used alone.

Asphalt tars contain a mixture of paraffinic and aromatic hydrocarbons and heterocyclic compounds containing sulfur, nitrogen, and oxygen. As a class, aromatic VP's are frequently not amenable to conventional pollution control treatments, at least within economically practical limits. The reduction of aromatic hydrocarbon concentrations requires relatively high initial VTA/C concentrations, and the pollution reducing reactions are notably promoted by incorporating metallic halides such as ferric chloride or ferric bromide in the treatment agent.

The VTA/C treatment of aromatic hydrocarbons such as benzene proceeds most efficiently in the presence of sunlight or other actinic light.

The VTA/C treatment of benzene and its homologs may be carried out in the dark provided that reaction promoters such as oligodynamic metals, free radical initiators, free radicals, or active forms of oxygen are present. Benzene may be treated with a VTA/C containing bromine as the active principle in sunlight. However, in the absence of oxygen or another reaction promoter, treatment is difficult.

EXAMPLE VII

The tests described in EXAMPLE VI were repeated with unsaturated aliphatic and aromatic hydrocarbon—butadiene and benzene—VP's and VTA/C No. 7. That treatment agent was formulated as follows:

| Water | 95.0% |
|---|---|
| Hydrogen Iodide (as hydriodic acid) | 0.5% |
| Aluminum bromide | 0.5% |
| Sulfuric acid | 3.0% |
| Chlorine, 8% solution | 1.0% |
| Total | 100.0% |

Reductions in VP concentration were: benzene, 130 ppm to 27 ppm; butadiene, 145 ppm to 21 ppm.

EXAMPLE VIII

Municipal compost leachates giving off vapors with high levels of oxidized fatty acids and amines were treated with a variety of VTA/C's employing the principles of the present invention using the equipment and procedure described in EXAMPLE IV except that the forced air was passed through a flask to which the leachate sample had been added.

The VTA/C's and the results that were obtained are described below.

VTA/C No. 8

Formulation:

Aluminum trichlorohydrate $[Al_2(OH)_5Cl]_3$, 5 gms

Atlas G-3300 anionic detergent, 2.5 gms

GE Silicone 220, 2.5 gms

Tap water (pH 4.5), 500 ml

VP Removal Efficiency: 80.0 percent to 84.0 percent.

An addition of 0.25% bromine as bromine chloride produced an additional 75% reduction in VP concentration.

An addition of dilute hydrochloric acid to VTA/C No. 8 during scrubbing resulted in an immediately noticeable loss of efficiency. An addition of 1% concentration of 42% hydrobromic acid improved the VP reduction to 99.9%.

VTA/C No. 9

Formulation:
Same as VTA/C No. 8 with Van-Wet 9N9 nonionic detergent substituted for the Atlas G-3300.
Removal Efficiency: 99.2 percent to 99.5 percent.

VTA/C No. 10

Formulation:
Same as VTA/C No. 8 except that Bio-Dac cationic detergent was used.
Removal Efficiency: 99.4 percent to 99.7 percent.

VTA/C No. 11

Formulation:

Same as VTA/C No. 8 except that aluminum chlorohydrate was substituted for the aluminum trichlorohydrate on an equimolar basis.

Removal Efficiency: 91.2 percent to 92.6 percent.

VTA/C No. 12

Formulation:

An equimolar substitution of zirconyl chloride for the aluminum trichlorohydrate used in VTA/C No. 8 was made.

Removal Efficiency: 75.0 percent to 89.0 percent.

The addition of 1% chlorine (8% solution) increased the VP removal efficiency to 89%. The addition of 0.5% bromine as bromoacetic acid increased the VP removal efficiency to 99.9%.

VTA/C No. 13

Formulation:

An equimolar substitution of aluminum zirconium tetrachlorhydrate for the aluminum trichlorohydrate used in VTA No. 8 was made.

Removal Efficiency: 83.0 percent to 99.6 percent.

VTA/C No. 14

Formulation:

An equimolar substitution of zirconium oxychloride for the aluminum trichlorohydrate used in VTA/C No. 8 was made.

Removal Efficiency: 97.7 percent to 98.2 percent (92.2 percent to 93.5 percent with dilute, 0.005% hydrobromic acid present in the reaction zone).

EXAMPLE IX

Terpenes and terpenoids, both derivatives of isoprenes, comprise a substantial class of widely distributed compositions. While frequently desirable commodities of commerce, they are sometimes released into the air from different manufacturing processes. In such circumstances, these compounds become pollutants.

Tests as described in EXAMPLE I were repeated, using a 50/50 mixture of water and turpentine metered through a peristaltic pump at the rate of 20 mls per minute onto the hot surface of a rotating dryer set at 350° F. as a VP-contaminated test stream.

The treatment agent (VTA/C No. 15) was formulated as follows:

| | |
|---|---|
| Carrier (water) | 96.50% |
| Solvents | |
| alcohol | 0.45% |
| acetic acid | 0.55% |
| Aluminum bromide | 0.50% |
| Hydrogen peroxide (10% solution) | 1.00% |
| Bromine and chlorine as 1-bromo-3-chloro-5,5-dimethylhydantoin | 2.00% |
| Total | 100.00% |

Results by scanning IR at an analytical wavelength of 3.4:

| | VP Concentration (ppm) |
|---|---|
| Before treatment | 390 |
| After treatment with VTA/C No. 15 | 75 |
| After treatment with VTA/C No. 15 in a reaction zone exposed to actinic radiation (250 watt halide lamp) | 20 |

Alternatives that can be employed with comparable results include:

- the use of actinic radiation from natural sunlight or a sodium vapor lamp,
- the inclusion of pyridine in the solvent constituent of the VTA/C,
- the replacement of all or part of the aluminum bromide with aluminum chloride or zinc and copper bromides and chlorides, and
- the addition of an oxidizing agent—for example, air, [O], $O_2$, $O_3$, benzoyl peroxide, or hydrogen peroxide.

The dryer contaminated the effluent with 128 ppm of carbon monoxide. The concentration of this pollutant was reduced to 59 ppm in the treatment zone. Also, the concentration of carbon dioxide in the test effluent was reduced by 10 percent.

EXAMPLE X

Production scale tests of various VTA/C's on VP-containing effluents were made at the Louisiana-Pacific Oriented Strand Board Plant at Corrigan, Tex. The tests were conducted by Environmental Monitoring Labs.

The source of the VP-contaminated emissions, treated with the goal of reducing VP concentration, was a rotary dryer used to dry southern pine wood wafers from a moisture content of 50% to a final moisture content of 6–7%. Heat was supplied by a wood-fired suspension burner. The air flow was approximately 45,000 acfm at 230° F.

The pilot emission treatment plant consisted of two Dynawave reverse jet scrubbers in series with a common induction fan. The air flow through the test units was about 270 acfm at 160° F.

TEST RUN #1

Two and one-half percent (2.5%) of 1-bromo-3-chloro-5,5-dimethylhydantoin (BCDMH) and 2.5% of aluminum chlorohydrate in a 50 percent aqueous solution and 1% of acetic acid were mixed in the sump of the first reverse jet with 60 gallons of water.

The run began at 11:05 P.M. Samples taken over the course of the test showed the following reductions in VP concentration: from 325 ppm to 70 ppm; from 180 ppm to 35 ppm; from 160 ppm to 38 ppm.

The air flow was increased to 375 acfm with the outlet VP concentration rising from 42 ppm to 65 ppm. With the air flow adjusted back to 270 acfm, the outlet VP concentration was 53 ppm. Continuing testing showed a reduction in VP concentration from 240 ppm to 58 ppm.

The second jet, filled with water, was activated at 3:04 P.M. with recirculation between the sumps. This resulted in a 180 ppm to 70 ppm reduction of VP's. Finally, the air flow was reduced from 350 acfm to 285 acfm and then restored to 350 acfm. This resulted in a change of VP concentration from 86 ppm to 81 ppm and back to 86 ppm.

Dryer conditions: 875° F. inlet temperature, 250° F. outlet temperature, inlet wood moisture 49.6%, outlet wood moisture 6.2%, feed rate control setting —3.00, opacity 10%.

Dynawave conditions: first jet—pH 3.57, temperature 134° F.; RJ nozzle—15 psig, L/G 45, air flow 350 acfm; second RJ nozzle—15 psig.

TEST RUN #2

0.6% of BCDMH, 0.6% of aluminum chlorohydrate in a 50% aqueous solution, and 0.3% of acetic acid were mixed in 40 gallons of water by sequential additions with only the first jet activated. The run began at 8:55 A.M. with only BCDMH. The inlet reading was 150 ppm VP's with the outlet at 60 ppm initially but rising to about 150 ppm. The aluminum chlorohydrate was added at 9:25 A.M. with no change noticed and the VP concentration still at 150 ppm. Acetic acid was added at 9:30 A.M., and a drop in VP concentration from 160 ppm to 140 ppm was seen. This depression lasted about 3 minutes. The outlet VP concentration returned to 160 ppm. The inlet VP concentration was again measured and found to be at 270 ppm. The test ended at 9:45 A.M.

Dryer conditions: 725° F. inlet, 250° F. outlet, inlet wood moisture 52.5%, outlet wood moisture 6.3%, feed rate control setting—3.00, opacity 6%.

Dynawave Conditions: first jet—pH 3.25, temperature 134° F.; RJ nozzle—18 psig, L/G 60, air flow 270 acfm; second RJ nozzle—off.

TEST RUN 3

0.6% of BCDMH, 0.6% of aluminum chlorohydrate in a 50 percent aqueous solution, and 0.3% of acetic acid were mixed in 40 gallons of water by sequential additions with only the first jet activated. The second reverse jet pump was connected to the first stage sump and used as an agitation pump to keep the contents of the first stage sump thoroughly mixed. The run began at 12:48 P.M. with the BCDMH producing a reduction in VP concentration of from 190 ppm to 60 ppm. The aluminum chlorohydrate was added at 12:55 A.M. with no additional reduction observed. The acetic acid was added at 1:00 P.M. with no additional reduction observed. The run was continued until 2:40 P.M. The outlet VP concentration was initially constant at 60 ppm with a slow upward trend toward 90 ppm. The inlet VP concentration, checked at 2:33 P.M., was at 170 ppm. The test ended at 2:40 P.M.

Dryer conditions: 725° F. inlet, 250° F. outlet, inlet wood moisture 50.5%, outlet wood moisture 6.5%, feed rate control setting—3.00, opacity 5%.

Dynawave Conditions: first jet—pH 3.1, temperature 135° F.; RJ nozzle—20 psig, L/G 65, air flow 270 acfm; second RJ nozzle—off.

TEST RUN #4

0.6% of BCDMH, 0.6% of aluminum chlorohydrate in a 50 percent aqueous solution, and 0.3% of acetic acid were mixed in 40 gallons of water by sequential additions with the first jet activated with agitation. The run began at 3:13 P.M. with the BCDMH producing a reduction of VP concentration from 150 ppm to 80 ppm. The aluminum chlorohydrate was added at 3:33 P.M. with a reduction in VP concentration from 80 ppm to 68 ppm. This reduction lasted about 4 minutes, then rising to 75 ppm and settling at 70 ppm. This emission rate remained constant for about 15 minutes when a slow upward trend developed. When the outlet VP concentration reached 90 ppm at 3:53 P.M., the acetic acid was added. This resulted in a depression of the VP concentration to 65 ppm. The inlet was reading 170 ppm at this time. The test ended at 4:20 P.M.

Dryer conditions: 800° F. inlet, 250° F. outlet, inlet wood moisture 50.3%, outlet wood moisture 6.1%, feed rate control setting—3.00, opacity 5%.

Dynawave Conditions: first jet—pH 3.10, temperature 135° F.; RJ nozzle—20 psig, L/G 65, air flow 270 acfm; second RJ nozzle—off.

TEST RUN #5

2.5% of BCDMH, 2.5% of aluminum chlorohydrate in a 50 percent aqueous solution, and 1.0% of acetic acid were mixed in 40 gallons of water by sequential additions with the first and second jets activated with agitation. The run began at 6:15 P.M. and was halted at 6:45 P.M. because of plant production problems. The BCDMH solution was left in the sump overnight, and the test was restarted at 8:45 A.M. after 30 minutes of sump mixing. The BCDMH produced a VP concentration reduction from 85 ppm to 15 ppm. The aluminum chlorohydrate was added at 9:12 A.M. with a VP concentration reduction of 17 ppm to 15 ppm. The acetic acid was added at 9:32 A.M. This resulted in an 8 minute depression in VP concentration from 45 ppm to 35 ppm. The outlet concentration remained at 45 ppm. The inlet reading was 350 ppm at this time.

The second jet was turned off at 9:58 P.M., and the outlet ppm of VP's rose from 50 to 72. The second jet was turned back on at 10:02 P.M., resulting in a reduction from 72 to 45 ppm. The inlet was again checked and found to be running at 250 ppm. The test ended at 10:17 P.M.

Dryer conditions: 615° F. inlet, 240° F. outlet, inlet wood moisture 50.4%, outlet wood moisture 5.8%, feed rate control setting—3.05, opacity 5%.

Dynawave Conditions: first jet—pH 3.10, temperature 134° F.; RJ nozzle—18 psig, L/G 60, air flow 270 acfm; second RJ nozzle—off.

TEST RUN #6

6.0% of bromyl alkyl amide, 2.5% of aluminum chlorohydrate in a 50 percent aqueous solution, and 2.5% of acetic acid were mixed in 40 gallons of water by sequential additions with the first and second jets operational and activated with agitation. The run began at 11:47 A.M. The VTA/C produced a reduction in VP concentration of from 140–150 ppm to 45–37 ppm. The aluminum chlorohydrate was added at 12:11 P.M. with a reduction in VP concentration to 24 ppm. The acetic acid was added at 12:29 P.M. This resulted in the VP concentration increasing from 25 ppm to 31 ppm and then leveling at 28 ppm. At 2:10 P.M., an additional 2.5% of aluminum chlororhydrate was added with no effect seen. The outlet VP concentration remained at 30–40 ppm until the test ended at 3:30 P.M.

Dryer conditions: 745° F. inlet, 240° F. outlet, inlet wood moisture 49.6%, outlet wood moisture 5.8%, feed rate control setting—3.05, opacity 5%.

Dynawave Conditions: first jet—pH 3.25, temperature 131° F.; RJ nozzle—20 psig, L/G 65, air flow 270 acfm; second RJ nozzle—temperature 115° F., L/G 70.

TEST RUN #7

133,447 grams of a 38% solution of sodium bromide was added to 15 gallons of water in the first stage of the pilot plant. The second stage was operated independently with 15,084 grams of sodium hydroxide added to 45 gallons of water. The run began at 4:48 P.M. with the inlet reading 170 ppm VP'S. The outlet VP concentration began at 170 ppm and gradually decreased to 34 ppm at 6:05 P.M. At 5:15 P.M. 2.5 % of aluminum chlorohydrate was added with no effect seen. The test was halted at 6:10 P.M.

Dryer conditions: 775° F. inlet, 240° F. outlet, inlet wood moisture 42.0%, outlet wood moisture 5.5%, feed rate control setting—3.20, opacity 7%.

Dynawave Conditions: first jet—pH x.xx, temperature 140° F.; RJ nozzle—20 psig, L/G xx, air flow 270 acfm; second RJ nozzle—temperature 132° F., L/G 70; RJ nozzle—116 psig.

TEST RUN #8

5.0% of BCDMH, 5.0% of aluminum chlorohydrate in a 50 percent aqueous solution, and 2.0% of acetic acid were mixed in 40 gallons of water by sequential additions with the first and second jets activated with agitation. Mixing of the VTA/C was continued for 30 minutes prior to the start of the run. The run began at 9:35 A.M. with the VTA/C reducing the VP concentration from 150 ppm to 27 ppm. The aluminum chlorohydrate was added at 11:45 P.M. with no further reduction seen. The acetic acid was added at 12:16 P.M.; no result was seen. Final inlet and outlet VP concentrations were 220 ppm and 31 ppm, respectively. The test ended at 12:31 P.M. when a recirculation hose ruptured.

Dryer conditions: 750° F. inlet, 240° F. outlet, inlet wood moisture 44.0%, outlet wood moisture 6.4%, feed rate control setting—3.20, opacity 6%.

Dynawave Conditions: first jet—pH x.xx, temperature 131° F.; RJ nozzle—20 psig, L/G 65, air flow 270 acfm; second RJ nozzle—off.

TEST RUN #9

2.50% of BCDMH, 2.50% of aluminum chlorohydrate in a 50 percent aqueous solution, and 1.0% of acetic acid were mixed in 40 gallons of water by sequential additions with the first and second jets activated with agitation. Mixing of the VTA/C was continued for 30 minutes prior to the start of the run. The run began at 10:00 A.M. with the VTA/C reducing the VP concentration from 400 ppm to 70 ppm. The aluminum chlorohydrate was added at 10:42 A.M. with a reduction in VP concentration from 80 to 70 ppm seen. The acetic acid was added at 12:54 P.M., and a drop in VP concentration from 70 ppm to 60 ppm was seen. Average inlet and outlet concentrations were 280 ppm and 70 ppm, respectively. At the end of the run the weir bowl was turned off, resulting in an increase of VP concentration in the outlet from 50 ppm to 90 ppm. When the bowl was turned back on, the outlet concentration returned to 50 ppm. The test ended at 6:15 P.M.

CO was reduced in this run from 162 to 79 ppm, and $CO_2$ was reduced from 1.4 to 1.1%.

Dryer conditions: 875° F. inlet, 255° F. outlet, inlet wood moisture 50.8%, outlet wood moisture 5.7%, feed rate control setting—3.40, opacity 12%.

Dynawave Conditions: first jet—pH 2.65, temperature 132° F.; RJ nozzle—20 psig, L/G 65, air flow 266 acfm; second RJ nozzle—xxx.

TEST RUN #10

6.0% of bromyl alkyl amide and 2.5% of aluminum chlorohydrate in a 50 aqueous solution were mixed in 43 gallons of water by sequential additions with the first and second jets operational and activated with agitation. The run began at 9:13 A.M. The VTA/C reduced the VP content from 355 to 30 ppm. The aluminum chlorohydrate was added at 9:36 A.M., reducing the VP content from 280 to 20 ppm. The outlet VP concentration remained at 30–40 ppm until the test ended at 2:01 P.M.

CO was reduced from 137 to 78 ppm, and $CO_2$ was reduced from 1.1 to 0.8%.

Dryer conditions: 800° F. inlet, 240° F. outlet, inlet wood moisture 48.1%, outlet wood moisture 5.9%, feed rate control setting—3.20, opacity 10%.

Dynawave Conditions: first jet—pH 3.62, temperature 132° F.; RJ nozzle—20 psig, L/G 65, air flow 270 acfm; second RJ nozzle—temperature 132° F., L/G xx; RJ nozzle—20 psig.

TEST RUN #11

2.50% of BCDMH, 2.50% of aluminum chlorohydrate in a 50 percent aqueous solution, and 1.0% of acetic acid were mixed in 40 gallons of water by sequential additions with the first and second jets activated with agitation. Mixing of the VTA/C was continued for 30 minutes prior to the start of the run. The run began at 7:50 P.M. with the VTA/C reducing the VP concentration from 200 ppm to 15 ppm. The aluminum chlorohydrate was added at 8:13 P.M. with a reduction of 15 to 10 ppm seen. The acetic acid was added at 8:43 P.M.; no effect was seen. Average inlet and outlet VP concentrations were 200 ppm and 20 ppm, respectively. At the end of the run the nozzle pressure was cycled between 10 and 20 psig. No real effect was seen. After the run was "officially over," the inlet VP concentration was increased to 400 and then to 450 ppm. The outlet VP concentration tracked the inlet VP concentration, rising to 140 ppm at its highest point.

Dryer conditions: 840° F. inlet, 240° F. outlet, inlet wood moisture 47.6%, outlet wood moisture 6.0%, feed rate control setting—3.15, opacity 11%.

Dynawave Conditions: first jet—pH 2.65, temperature 132° F.; RJ nozzle—20 psig, L/G 65, air flow 266 acfm; second RJ nozzle—xxx.

In the equipment employed in Runs 1–11, the actual feed rates corresponding to the control settings (3.00 to 3.40) correspond to approximate feed rates of the wood wafers ranging from 9000 to 13000 O.D. lb/hr.

Values identified by x's mean that no measurement was made or that the value was otherwise not available.

EXAMPLE XI

Styrene, acronitrile resin, and butadiene were individually processed through the system described in EXAMPLE I. The rate of VP-contaminated ambient air flow was approximately 200 acfm. The VP concentration was reduced from 325 ppm by treatment with VTA/C No. 15 to about 35 ppm. Exposing the reaction zone to the actinic radiation from a 500 watt sodium vapor lamp resulted in an additional VP reduction to 1 to 2 ppm as measured by FID.

This ability of the present invention to reduce the concentration of styrene in styrene-contaminated gas streams, typically by at least an order of magnitude, is of singular importance. By volume, styrene is the twentieth most used chemical in the United States. It is employed to manufacture such diverse products as boat hulls, trailers, automotive and other components, shower stalls, sinks, and bathtubs, to mention just a few. Styrene vapors are evolved during the "set-up" and "curing" of such items, and workers are exposed to considerable concentrations of those vapors. In order to reduce this exposure, workspaces are ventilated to the out-of-doors, often creating a serious air pollution problem.

EXAMPLE XII

The tests described in this example employed the decontamination system described in EXAMPLE III. The 10-gallon fiber drum 20 was filled with fresh compost material—grass, hedge trimmings, chopped leaves, twigs, branches, and the like. The IR scan had a strong peak at 9.5 pm, using a 20.25 $\mu$m IR transmission path length. The effluent-measured IR transmission corresponded to 385 ppm of VP's in untreated effluent from the drum. VP's in the treated effluent were approximately 0.9 ppm. The reduction in the concentration of VP's was over 99 percent.

Also, ten adult subjects were used to determine VP aromatic characteristic and intensity. The subjects were evenly divided between men and women.

Sniff tests were made after force heating the drum contents with the hair dryer 24 for 15 minutes. Descriptions of the odor of the untreated effluent in descending order by number of subjects were: sour, green, rotten grass. On an ascending scale of 1 to 10, the average rating for intensity was 8. For unpleasantness, the rating was 8 on the same 1–10 ascending scale.

Repetition of the test after the effluent was scrubbed in blender 42 with VTA/C No. 1 yielded the following average results: character, mild; intensity, average=1.5; unpleasantness, average=1.

EXAMPLE XIII

Figure 2:
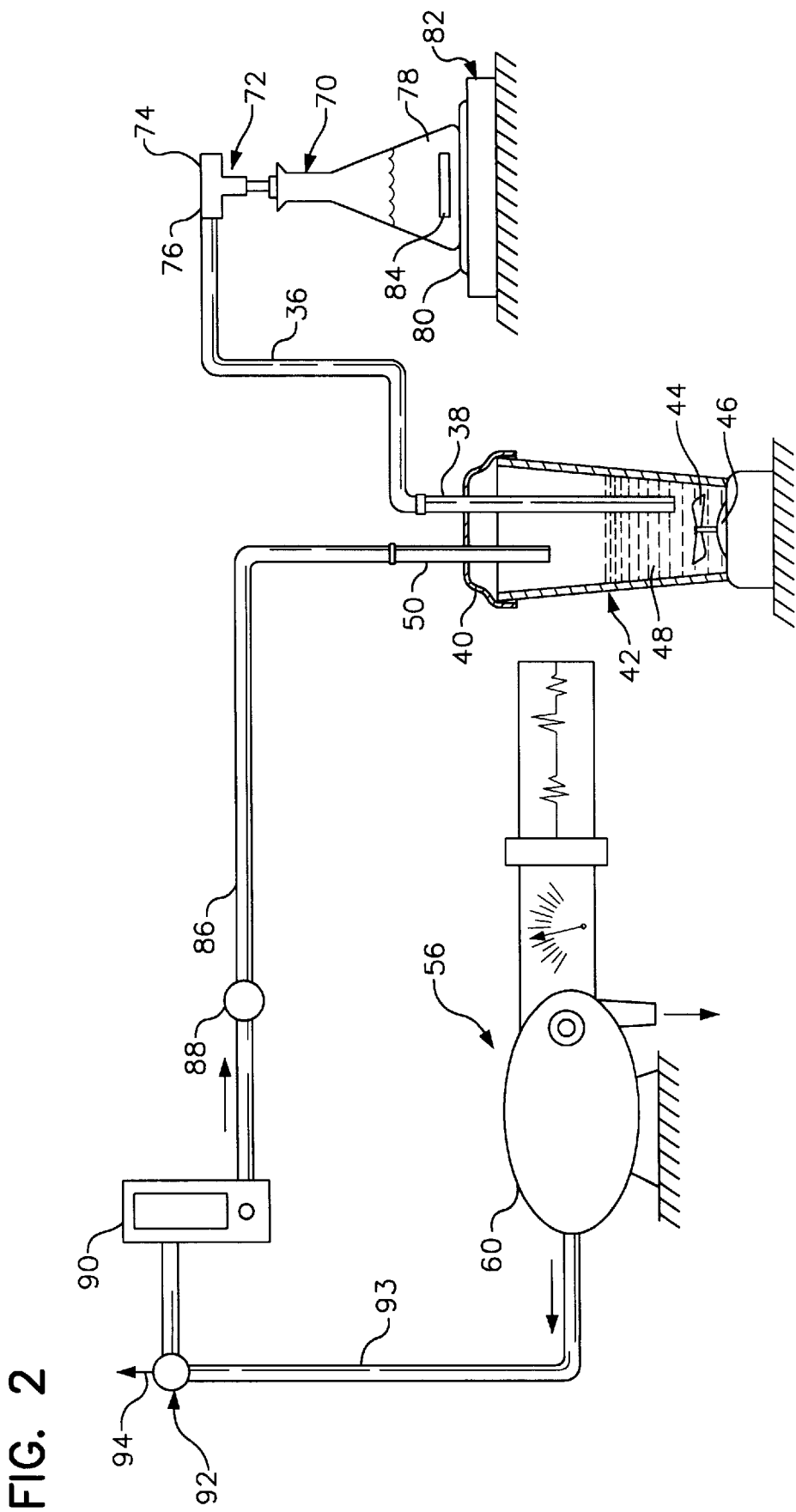
FIG. 2 is a like schematic of a second system which can be employed for the same purpose.

The tests reported in this example used the apparatus described in EXAMPLE III with the following changes (shown in FIG. 2). A one thousand ml Ehrlmeyer flask 70 was substituted for the fiber drum 20; a number eight stopper 72 with an inlet 74 and an outlet 76 was used to seal the mouth of the flask after filling the flask with 500 mls of aged mixed herring and salmon oil 78; the flask 70 was placed on the pad element 80 of a Magnamixer hot plate 82 set at 250° F.; a 2-inch magnetic stir bar 84 was dropped into the flask; and the stir bar was rotated at medium speed (about 200 RPM) by a conventional, motor driven, rotating magnet (not shown). The stopper outlet 76 was connected by way of blender 42 and Teflon tubes 36 and 86 to the vacuum side of a one-eighth horsepower, diaphragm type vacuum/pressure pump 88. The pressure side of pump 88 was connected to a flow meter 90, and the flow meter was connected to a three-way valve 92. One outlet port of the three-way valve was affixed to plenum 60 of IR scanner 56 by Teflon tube 93. The other port 94 was used for sniffing.

The scanning IR 56 showed a strong 9.7 $\mu$m peak corresponding to triethylamine, using a 20.27 $\mu$m IR transmission pathlength. The concentration of triethylamine in untreated effluent from the flask 70 corresponded to approximately 150 ppm. Treated, the concentration was approximately 13 ppm.

EXAMPLE XIV

Five hundred mls of mixed fatty acids—acetic, butyric, valeric, caproic, caprylic, cetoleic, eicosapentaenoic and docosahexanenoic—were tested according to the EXAMPLE XIII protocol. The Magnamixer hot plate 82 was turned down to 150° F.

The IR scanner 56 displayed a peak at 8.6 $\mu$m with a 20.25 $\mu$m pathlength corresponding to acetic acid. A peak of 9.6 $\mu$m at a 20.25 $\mu$m pathlength was selected as indicative of the presence of other acids in the mixture. Untreated effluent showed a VP concentration of approximately 165 ppm at 8.6 $\mu$m and 123 ppm at 9.6 $\mu$m. The treated effluent showed concentrations of only 9 ppm and 6 ppm, respectively, for acetic acid and for acids with a peak at 9.6 $\mu$m.

EXAMPLE XV

Figure 3:
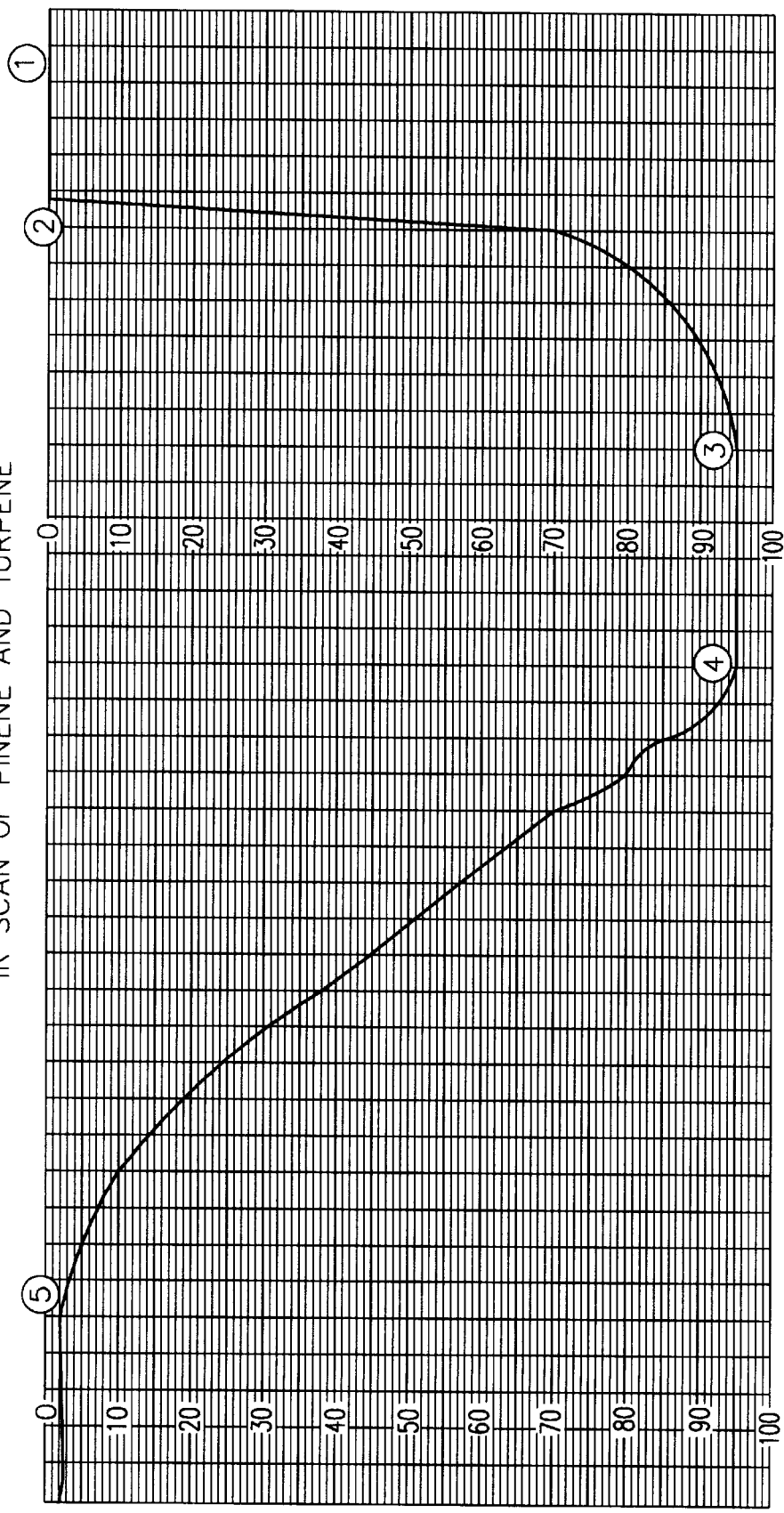
FIG. 3 is a trace generated by an IR scan of an untreated sample containing pinene and terpene.
Figure 4:
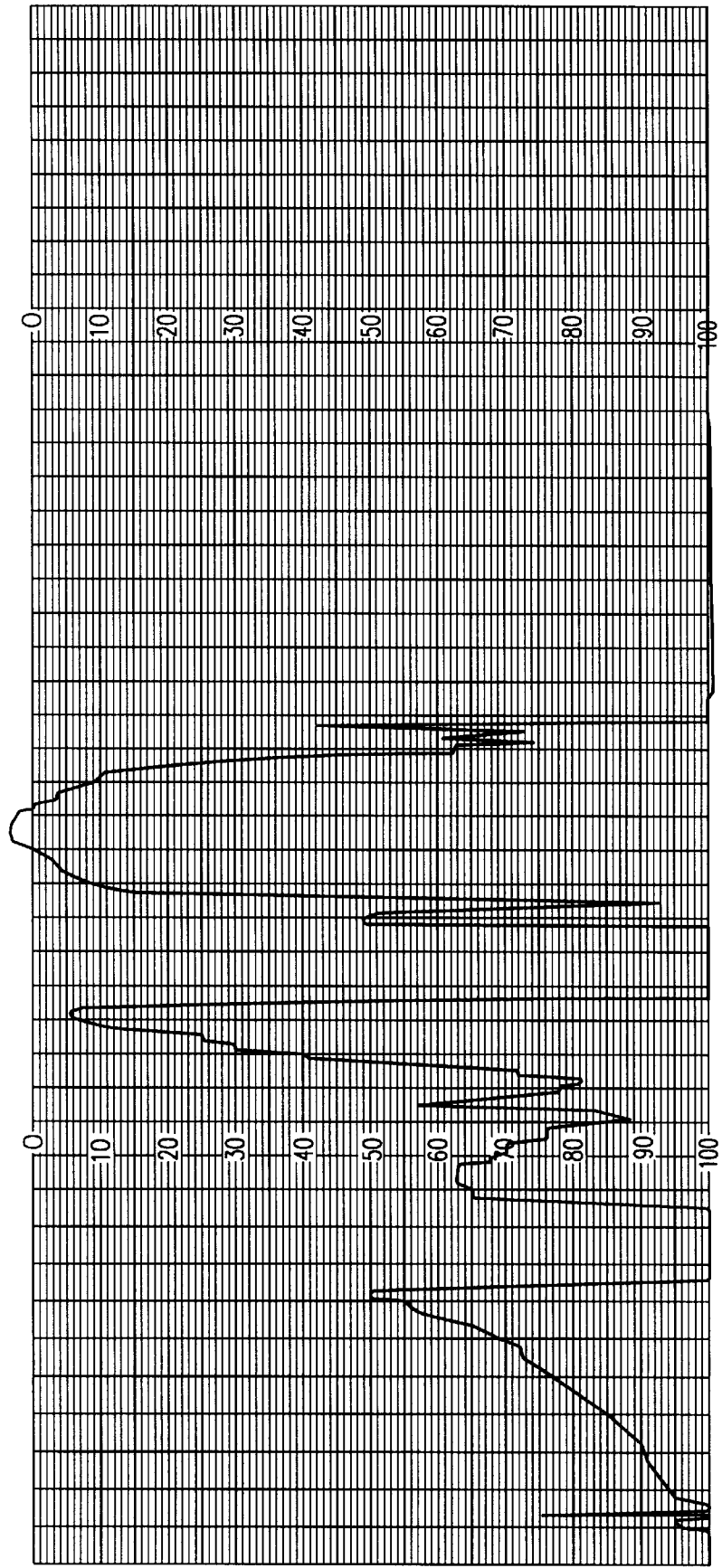
FIG. 4 is a scan of the same sample after it was treated with a VTA/C formulated in accord with the principles of the present invention.
Figure 5:
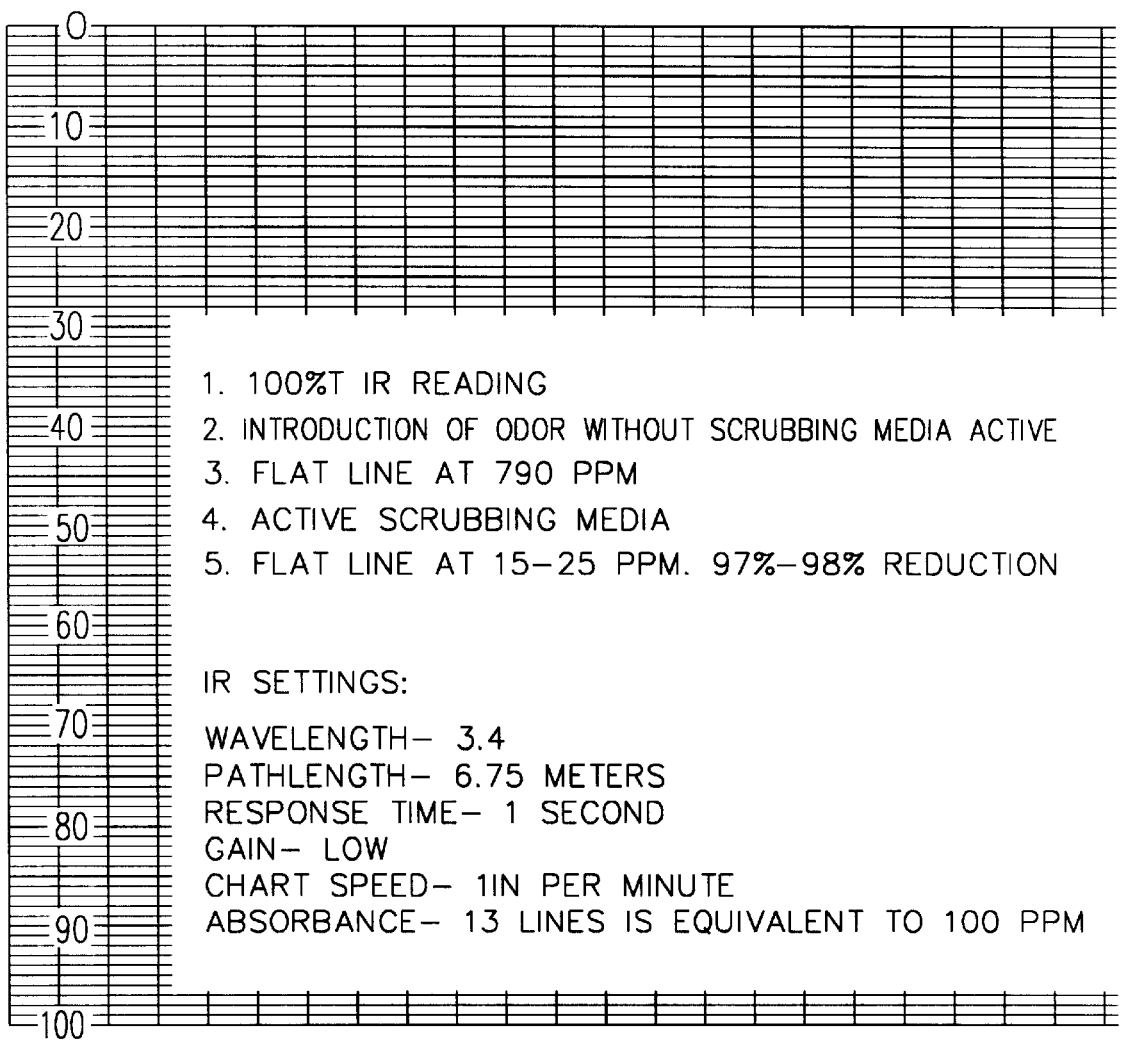
FIG. 5 is a table of information for interpreting FIGS. 3 and 4.

FIGS. 3 and 4 depict graphically representative results obtained by scrubbing an air stream containing pinene and terpene with an aqueous aluminum chlorohydrate and aluminum bromate scrubbing medium in a Waring blender as discussed above in EXAMPLE I. This resulted in the concentration of those VP's in the sample being reduced from 730 ppm to only a few parts per million.

Figure 6:
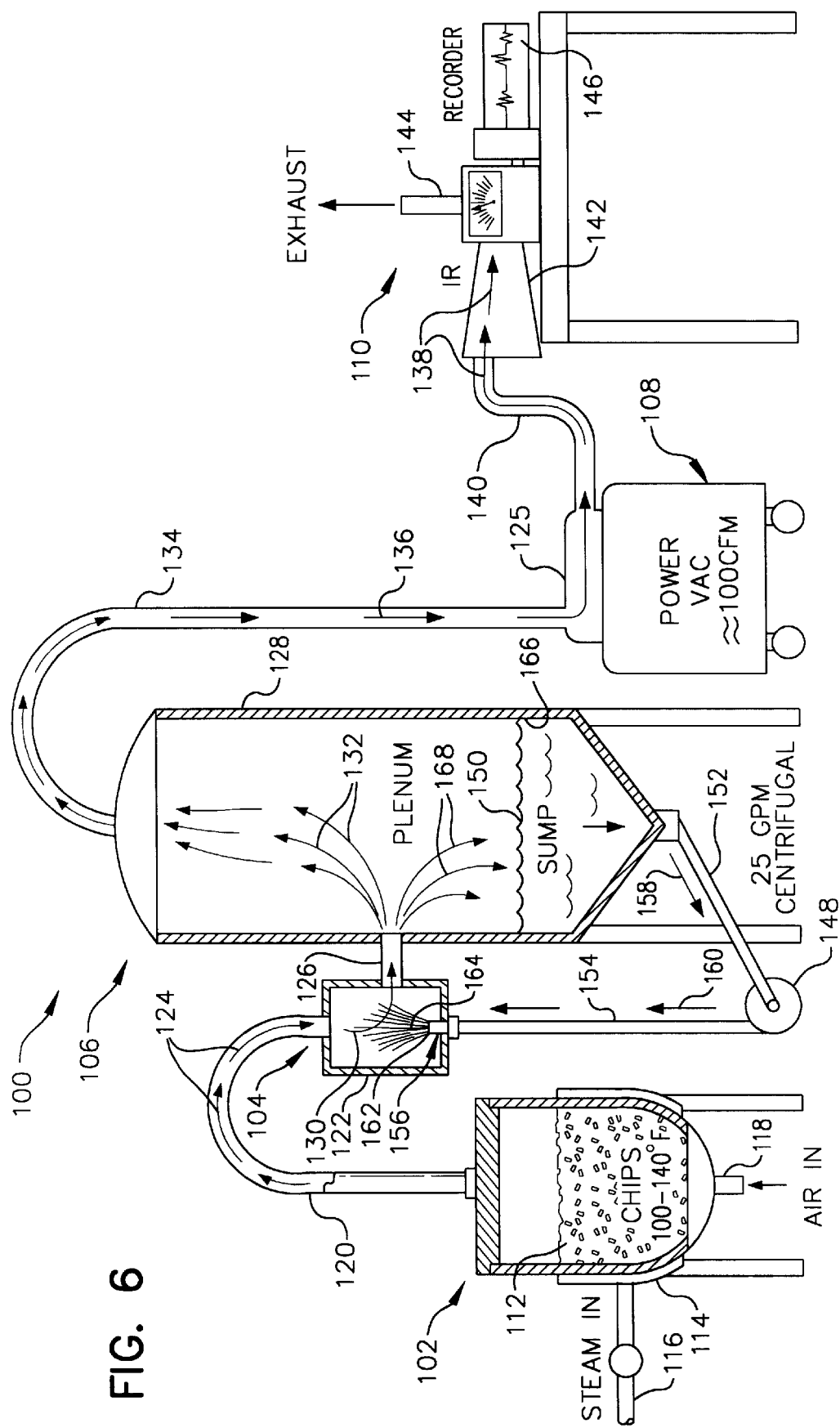
FIG. 6 is a schematic illustration of a third, larger scale system for treating VP's in accord with the principles of the present invention.

As discussed in the foregoing examples, VP devolatization processes can be carried out in the systems shown in FIGS. 1 and 2. One larger scale system is described in EXAMPLE X. A second large scale system is depicted in FIG. 6 and identified by reference character 100.

System 100 includes a jacketed kettle 102, a scrubbing unit 104, a scrubbing medium reservoir and recovery unit 106, a vacuum unit 108, and an IR scanner 110.

In the illustrated application of system 100, the jacketed vessel 102 is filled with wood chips 112. Steam is then introduced into the jacket 114 of the vessel through line 116 to heat wood chips 112 to a temperature in the range of 100–140° F. As wood chips 112 are heated, VP's are driven off.

The VP's are entrained in air introduced into vessel 102 through inlet line 118 and flow upwardly through the bed of chips 112.

The mixture of air and entrained VP's flows from vessel 102 through an offtake line 120 and is discharged downward into the casing 122 of scrubber unit 104 as indicated by arrows 124, the gas mixture being pumped along this path by the pump 125 in vacuum unit 108. That unit may be a conventional industrial vacuum cleaner of the wet/dry type.

Figure 7:
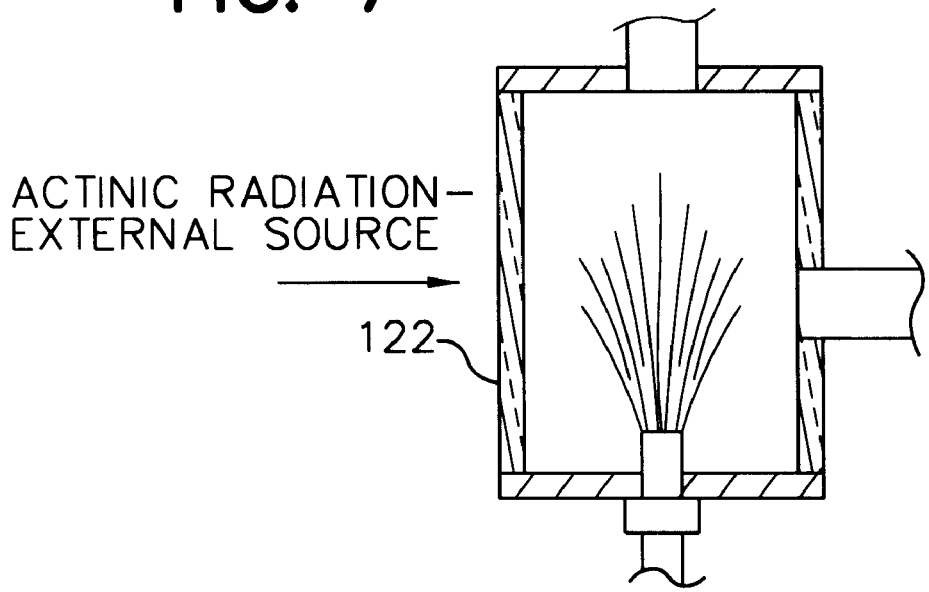
FIG. 7 is a generally pictorial view of a second type of scrubbing unit or reactor which can be employed in the VP devolatization system illustrated in FIG. 6.
Figure 8:
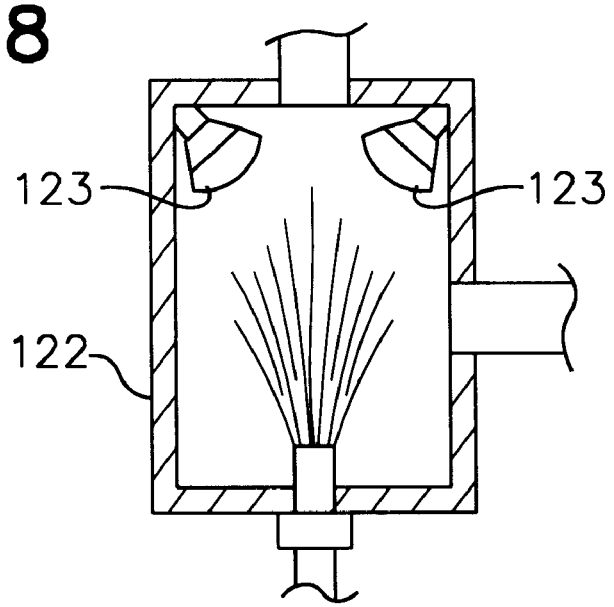
FIG. 8 is an also generally pictorial view of a third form of scrubbing unit or reactor for the FIG. 6 devolatization system.

In those applications of the present invention in which actinic radiation is employed to promote VTA/C-VP devolatization reactions, scrubber unit (or reactor) casing 122 can be fabricated—at least in part—of a material which will transmit the radiation to the interior of the unit from an exterior source (FIG. 7). Alternatively, the source can be located in the unit. This variation is shown in FIG. 8 in which the actinic radiation source consists of lamps identified by reference character 123.

To determine the efficiency of a scrubbing solution or VTA/C disclosed herein, it is necessary to first ascertain the concentration of the VP's in the air/VP's mixture before treatment. In furtherance of this objective, the mixture is simply pumped by vacuum unit 108 from scrubbing unit 104 through transfer line 126 into the tank or plenum 128 of reservoir/recovery unit 106 as shown by arrows 130 and 132.

From plenum 128, the untreated air/VP mixture flows through offtake line 134 to vacuum unit 108 as indicated by arrows 136 and then, as shown by arrows 138, through transfer line 140 into the plenum 142 of IR scanner 110. Analyzed gases are discharged from the scanner through exhaust 144, and results are displayed in the form of a trace on a strip chart 146.

Once the concentration of VP's in the untreated mixture has been measured in the manner just described, centrifugal pump 148 is turned on. This results in a VTA/C scrubbing medium 150 being pumped through a discharge line 152 and scrubbing unit inlet line 154 to a nozzle 156 as indicated by arrows 158 and 160. The outlet 162 of nozzle 156 is located in the lower reaches of scrubbing unit housing 122. Consequently, scrubbing medium pumped into the nozzle is formed by that component into an upwardly directed spray identified in FIG. 6 by reference character 164. This produces a countercurrent flow of the VP-contaminated air and scrubbing medium and a consequent efficient removal of the VP's from the air-based mixture.

The scrubbing medium with its burden of recovered VP's and the now decontaminated air flow through transfer line 126 into the plenum 128 of unit 106 as is also suggested by arrow 130. There, the spent scrubbing medium and its burden of recovered VP's falls to the sump 166 making up the lower part of plenum 128 as indicated by arrows 168. When the concentration of recovered VP's becomes too high, the scrubbing medium 150 in sump 166 can be removed for regeneration and replaced with fresh scrubbing medium.

The air from which the VP's have been stripped follows the path discussed above and delineated by arrows 132, 136, and 138 to the plenum 142 of IR scanner 110. The trace on the strip chart 146 outputted by that device will typically reflect an almost complete removal of the contaminated VP's from the air stream.

Commercially, a scrubber of the character depicted in FIG. 6 can be employed to separate the VTA/C-VP complexes from the air or other gas stream in which these complexes are entrained. Alternatively, the state-of-the-art, fluid injected, cyclone scrubber disclosed in U.S. Pat. No. 4,734,109 or any other appropriate type of scrubber may be used.

The VTA/C-VP complexes may contain resinous compounds. It was pointed out above that such resins may be collected by filters and gravity or other separators and disposed of or used as resins, fillers, or adhesives in a variety of processes. They may also be used as VTA/C constituents and in the regeneration and recycling of VTA/C's.

The VTA/C halogens and oligodynamic metals may as such be processed and recycled for use. For example, contact between a VTA/C and a substrate or VP may release a halogen such as bromine as a treatment byproduct. The halogen can be recovered in a number of ways. If, for example, the spent VTA/C-VP complexes are comprised of halogen and aliphatic or aromatic hydrocarbon compounds, they can be reacted with magnesium to form alkyl- and aryl-magnesium bromides. These bromides may be employed as intermediates for useful end products or even in VTA/C's for treating other VP's.

The invention may be embodied in many forms in addition to those discussed above without departing from the spirit or essential characteristics of the invention. The present embodiments are, therefore, to be considered in all respects as illustrative and not restrictive, the scope of the invention being indicated by the appended claims rather than by the foregoing description. All changes which come within the meaning and range of equivalency of the claims are therefore intended to be embraced therein.

What is claimed is:

1. A process for treating a gaseous or vaporous pollutant, said process consisting of:

exposing the gaseous or vaporous pollutant to a neutralizing composition in the presence of radiation having a wavelength greater than about 2100 Å, said neutralizing composition consisting of a bromine component selected from the group consisting of bromine, hydrobromic acid, aluminum bromide, zinc bromide. hydrogen bromide, bromine triflouride, ferric bromide, ferrous bromide, 1-bromo-3-chloro-5,5-dimethylhydantoin, bromine chloride, bromoacetic acid, copper bromide, bromyl alkyl amide, and sodium bromide; a chlorine component selected from the group consisting of chlorine, aluminum chloride, zinc chloride, allyl chloride, cobalt chloride, ferric chloride, aluminum chlorohydrate, aluminum trichlorohydrate, and hydrochloric acid;

alcohol;

and acetic acid.

2. A process for treating a gaseous or vaporous pollutant, said process consisting of:

exposing the gaseous or vaporous pollutant to a neutralizing composition in the presence of radiation having a wavelength greater than about 2100 Å, said neutralizing composition consisting of bromine component selected from the group consisting of bromine, hydrobromic acid, aluminum bromide, zinc bromide, hydrogen bromide, bromine triflouride, ferric bromide, ferrous bromide, 1-bromo-3-chloro-5,5-dimethylhydantoin, bromine chloride, bromoacetic acid, copper bromide, bromyl alkyl amide, and sodium bromide; a chlorine component selected from the group consisting of chlorine, aluminum chloride, zinc chloride, allyl chloride, cobalt chloride, ferric chloride, aluminum chlorohydrate, aluminum trichlorohydrate, and hydrochloric acid;

alcohol;

and pyridine.

3. A process for treating, a gaseous or vaporous pollutant, said process consisting of:

exposing the gaseous or vaporous pollutant to a neutralizing composition in the presence of radiation having a wavelength greater than about 2100 Å, said neutralizing composition consisting essentially of bromine component selected from the group consisting of bromine, hydrobromic acid, aluminum bromide, zinc bromide, hydrogen bromide, bromine triflouride, ferric bromine, ferros bromide, 1-bromo-3-chloro-5,5-dimethylhydantoin, bromine chloride, bromoacetic acid, copper bromide, bromyl alkyl amide,and sodium bromide; chlorine component selected from the group consisting of chlorine, aluminum chloride, zinc chloride, allyl chloride, cobalt chloride, ferric chloride, aluminum chlorohydrate, aluminum trichlorohydrate, and hydrocloric acid;

a silicon component;

and a surfactant.

* * * * *